(12) United States Patent
Yavorsky et al.

(10) Patent No.: US 9,029,517 B2
(45) Date of Patent: May 12, 2015

(54) CHROMATOGRAPHY MEDIA AND METHOD

(75) Inventors: David Yavorsky, Bolton, MA (US);
John Amara, Reading, MA (US);
Joaquin Umana, Stoneham, MA (US);
William Cataldo, Bradford, MA (US);
Mikhail Kozlov, Lexington, MA (US);
Matthew Stone, Cambridge, MA (US)

(73) Assignee: EMD Millipore Corporation, Billerica, MA (US)

( * ) Notice: Subject to any disclaimer, the term of this patent is extended or adjusted under 35 U.S.C. 154(b) by 151 days.

(21) Appl. No.: 13/191,992

(22) Filed: Jul. 27, 2011

(65) Prior Publication Data
US 2012/0029176 A1 Feb. 2, 2012

Related U.S. Application Data

(60) Provisional application No. 61/369,331, filed on Jul. 30, 2010.

(51) Int. Cl.
*B01J 20/28* (2006.01)
*B01J 47/12* (2006.01)
*C07K 1/18* (2006.01)
*C07K 1/20* (2006.01)
*C07K 1/22* (2006.01)
*B01D 15/32* (2006.01)
*B01D 15/36* (2006.01)
(Continued)

(52) U.S. Cl.
CPC .......... *B01D 15/327* (2013.01); *B01D 15/361* (2013.01); *B01D 15/3804* (2013.01); *B01J 20/28023* (2013.01); *B01J 20/285* (2013.01); *B01J 20/287* (2013.01); *B01J 20/3244* (2013.01); *C07K 1/18* (2013.01); *B01J 20/28059* (2013.01); *B01J 39/26* (2013.01); *B01J 41/20* (2013.01); *B01J 47/003* (2013.01); *B01J 47/123* (2013.01); *Y10S 502/52724* (2013.01)

(58) Field of Classification Search
None
See application file for complete search history.

(56) References Cited

U.S. PATENT DOCUMENTS 3,936,394 A   2/1976   Kusunose et al.
4,169,790 A   10/1979  Pretorius et al.
(Continued)

FOREIGN PATENT DOCUMENTS

CN   101617072 A   12/2009
CN   101768206 A   7/2010
(Continued)

OTHER PUBLICATIONS

U.S. Appl. No. 61/415,605, filed Nov. 19, 2010.*
(Continued)

*Primary Examiner* — Jeffrey E Russel
(74) *Attorney, Agent, or Firm* — Nields, Lemack & Frame, LLC

(57) ABSTRACT

Adsorptive media for chromatography, particularly ion-exchange chromatography, derived from a shaped fiber. In certain embodiments, the functionalized shaped fiber presents a fibrillated or ridged structure which greatly increases the surface area of the fibers when compared to ordinary fibers. Also disclosed herein is a method to add surface pendant functional groups that provides cation-exchange or anion-exchange functionality to the high surface area fibers. This pendant functionality is useful for the ion-exchange chromatographic purification of biomolecules, such as monoclonal antibodies (mAbs).

9 Claims, 14 Drawing Sheets

Surface modification of high surface area fibers with pendant sulfopropyl cation exchange functionality (SP) (a) allyl glycidyl ether, sodium hydroxide, sodium sulfate, water, 50 °C, 12 hours. (b) 2-acrylmido-2-methyl-1-propane sulfonic acid, N,N-dimethylacrylimide, water, ammonium persulfate, 80 °C, 4 hours.

(51) Int. Cl.
*B01D 15/38* (2006.01)
*B01J 20/285* (2006.01)
*B01J 20/287* (2006.01)
*B01J 20/32* (2006.01)
*B01J 39/26* (2006.01)
*B01J 41/20* (2006.01)
*B01J 47/00* (2006.01)

(56) References Cited

U.S. PATENT DOCUMENTS

| | | | |
|---|---|---|---|
| 4,384,957 A | | 5/1983 | Crowder, III et al. |
| 4,512,897 A | | 4/1985 | Crowder, III et al. |
| 4,657,742 A | | 4/1987 | Beaver |
| 4,675,104 A | | 6/1987 | Rai et al. |
| 4,721,572 A | | 1/1988 | Jordan |
| 5,162,074 A | | 11/1992 | Hills |
| 5,360,540 A | | 11/1994 | Andelman |
| 5,468,847 A | | 11/1995 | Heilmann et al. |
| 5,502,022 A | | 3/1996 | Schwarz et al. |
| 5,800,706 A | | 9/1998 | Fischer |
| 5,886,154 A | | 3/1999 | Lebing et al. |
| 5,906,747 A | | 5/1999 | Coffman et al. |
| 5,948,528 A | | 9/1999 | Helms, Jr. et al. |
| 6,008,036 A | * | 12/1999 | Fanget et al. ............ 435/239 |
| 6,228,995 B1 | | 5/2001 | Lee |
| 6,736,973 B1 | | 5/2004 | Podgornik et al. |
| 7,026,154 B1 | | 4/2006 | Gaillac et al. |
| 7,291,263 B2 | | 11/2007 | Ward et al. |
| 7,311,825 B2 | | 12/2007 | Shah |
| 7,465,397 B2 | | 12/2008 | Siwak et al. |
| 7,510,848 B2 | | 3/2009 | Hammond et al. |
| 7,517,381 B2 | * | 4/2009 | Rohrbach et al. ............ 55/524 |
| 8,137,561 B2 | | 3/2012 | Kozlov et al. |
| 8,722,757 B2 | * | 5/2014 | Janke et al. ............ 522/116 |
| 2002/0037565 A1 | | 3/2002 | Blanche et al. |
| 2002/0050470 A1 | * | 5/2002 | Jinno et al. ............ 210/198.2 |
| 2002/0058625 A1 | * | 5/2002 | Mitterer et al. ............ 514/12 |
| 2002/0177693 A1 | | 11/2002 | Lebing et al. |
| 2003/0127393 A1 | | 7/2003 | Tepper et al. |
| 2003/0146156 A1 | | 8/2003 | Siwak et al. |
| 2005/0023221 A1 | | 2/2005 | Marcus |
| 2005/0072737 A1 | | 4/2005 | Ward et al. |
| 2005/0080251 A1 | | 4/2005 | Lemmens |
| 2006/0003073 A1 | * | 1/2006 | Etzel et al. ............ 426/583 |
| 2006/0032816 A1 | | 2/2006 | Marcus et al. |
| 2006/0070950 A1 | | 4/2006 | Rasmussen et al. |
| 2006/0073527 A1 | * | 4/2006 | Albitar et al. ............ 435/7.23 |
| 2006/0275781 A1 | | 12/2006 | Pham et al. |
| 2007/0102363 A1 | * | 5/2007 | Little et al. ............ 210/656 |
| 2008/0105612 A1 | | 5/2008 | Chappas |
| 2008/0108265 A1 | | 5/2008 | Pourdeyhimi et al. |
| 2009/0130738 A1 | | 5/2009 | Kozlov |
| 2009/0176052 A1 | | 7/2009 | Childs et al. |
| 2010/0136025 A1 | | 6/2010 | Hickman et al. |
| 2010/0330119 A1 | | 12/2010 | Yamamoto et al. |
| 2011/0165645 A1 | | 7/2011 | Xiong |
| 2012/0148841 A1 | | 6/2012 | Pourdeyhimi et al. |
| 2012/0193278 A1 | | 8/2012 | Kozlov et al. |

FOREIGN PATENT DOCUMENTS

| | | |
|---|---|---|
| EP | 0269462 A2 | 6/1988 |
| EP | 1141249 A1 | 10/2001 |
| EP | 1796807 A2 | 6/2007 |
| EP | 2036584 A1 | 3/2009 |
| EP | 2087153 A2 | 8/2009 |
| EP | 2089563 A2 | 8/2009 |
| EP | 2266675 A2 | 12/2010 |
| EP | 2336304 A1 | 6/2011 |
| EP | 2346897 A2 | 7/2011 |
| EP | 2266675 A3 | 9/2011 |
| JP | 62-4440 A | 1/1987 |
| JP | 8-108069 A | 4/1996 |
| JP | 8-170958 A | 7/1996 |
| JP | 11-279945 A | 10/1999 |
| JP | 2000-504002 A | 4/2000 |
| JP | 2008-510142 A | 4/2008 |
| WO | 93/10899 A2 | 6/1993 |
| WO | 97/27844 A1 | 8/1997 |
| WO | 99/34916 A1 | 7/1999 |
| WO | 00/40702 A1 | 7/2000 |
| WO | 01/92552 A2 | 12/2001 |
| WO | 02/083893 A2 | 10/2002 |
| WO | 2005/021844 A2 | 3/2005 |
| WO | 2006/020640 A2 | 2/2006 |
| WO | 2008/006780 A1 | 1/2008 |
| WO | 2008/039136 A1 | 4/2008 |
| WO | 2008/057426 A2 | 5/2008 |
| WO | 2008/057431 A2 | 5/2008 |
| WO | 2009/146321 A1 | 12/2009 |
| WO | 2009/151593 A1 | 12/2009 |
| WO | 2010/036774 A1 | 4/2010 |
| WO | 2010/048192 A2 | 4/2010 |
| WO | WO 2010072381 A1 * | 7/2010 |
| WO | 2012/068442 A1 | 5/2012 |
| WO | 2014/120387 A1 | 8/2014 |

OTHER PUBLICATIONS

International Search Report and Written Opinion mailed Apr. 6, 2012 in corresponding PCT application No. PCT/US2011/045519.

Biotechnol. Prog. 2003, vol. 19, No. 2, pp. 464-468, "Recovery of *Acinetobacter radioresistens* Lipase by Hydrophobic Adsorption to n-Hexadecane Coated on Nonwoven Fabric", Wang, et al.

International Preliminary Report on Patentability mailed Feb. 14, 2013 in corresponding PCT application No. PCT/US2011/045519.

Organic Chemistry, 1st Edition, Oxford University Press: Oxford, 2001, pp. 203-204, Neutral oxygen bases, Clayden, et al.

AAPS PharmSciTech, vol. 12, No. 2, Jun. 2011, pp. 746-754, "Investigation into Stability of Poly(Vinyl Alcohol)-Based Opadry II Films", Koo, et al.

Principles of Biochemistry and Biophysics, 1st Edition, University Science Press, New Delhi, 2008, p. 31, Introduction to the Concepts of Chemistry, Chauhan.

Japanese Communication, with English translation, mailed Jan. 7, 2014 in corresponding Japanese patent application No. JP 2013-523201.

International Search Report and Written Opinion mailed Apr. 8, 2014 in co-pending PCT application No. PCT/US14/10158.

Chinese communication, with English translation, mailed Apr. 14, 2014 in corresponding Chinese patent application No. CN 201180037517.2.

Korean communication, with English translation, dated Dec. 1, 2014 in corresponding Korean patent application No. 10-2014-7025710.

Japanese communication, with English translation, dispatched Jan. 6, 2015 in corresponding Japanese patent application No. 2013-523201.

* cited by examiner

1(a)-c): A schematic illustration of fibers of the inventive concept. 1(d): SEM image of Allasso Industries Corporation winged fibers.

Surface modification of high surface area fibers with pendant sulfopropyl cation exchange functionality (SP) (a) allyl glycidyl ether, sodium hydroxide, sodium sulfate, water, 50 °C, 12 hours. (b) 2-acrylimido-2-methyl-1-propane sulfonic acid, N,N-dimethylacrylimide, water, ammonium persulfate, 80 °C, 4 hours.

FIG. 1f

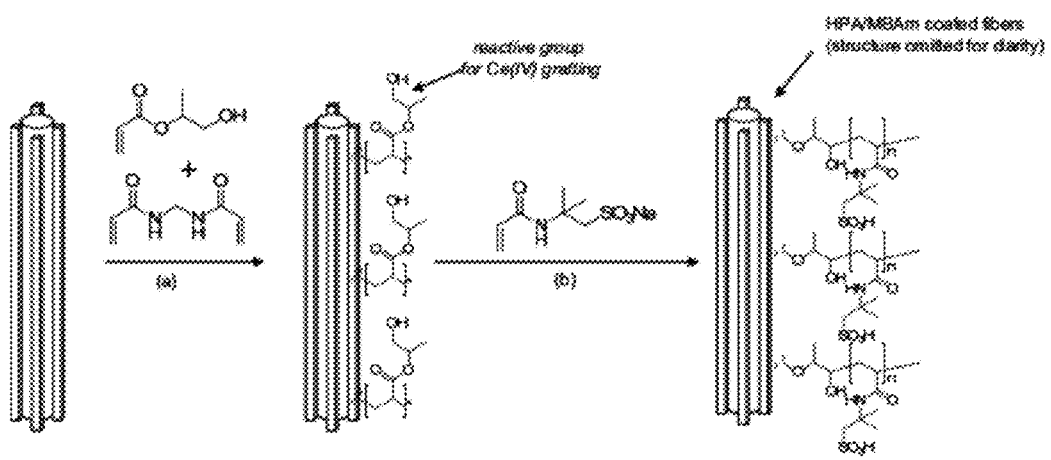

Surface modification of high surface area fibers with a pendant sulfopropyl cation exchange tentacle functionality (a) hydroxypropylacrylate, N,N'-methylenebis(acrylamide), ammonium persulfate, water, 80 °C, 4 hours. (b) 2-acrylamido-2-methyl-1-propanesulfonic acid sodium salt, water, ammonium cerium(IV) nitrate, $HNO_3$, 35 °C, nitrogen, 18 hours. *Note.* In the third graphic, the structure of the cross-linked HPA/MBAm coating is not shown.

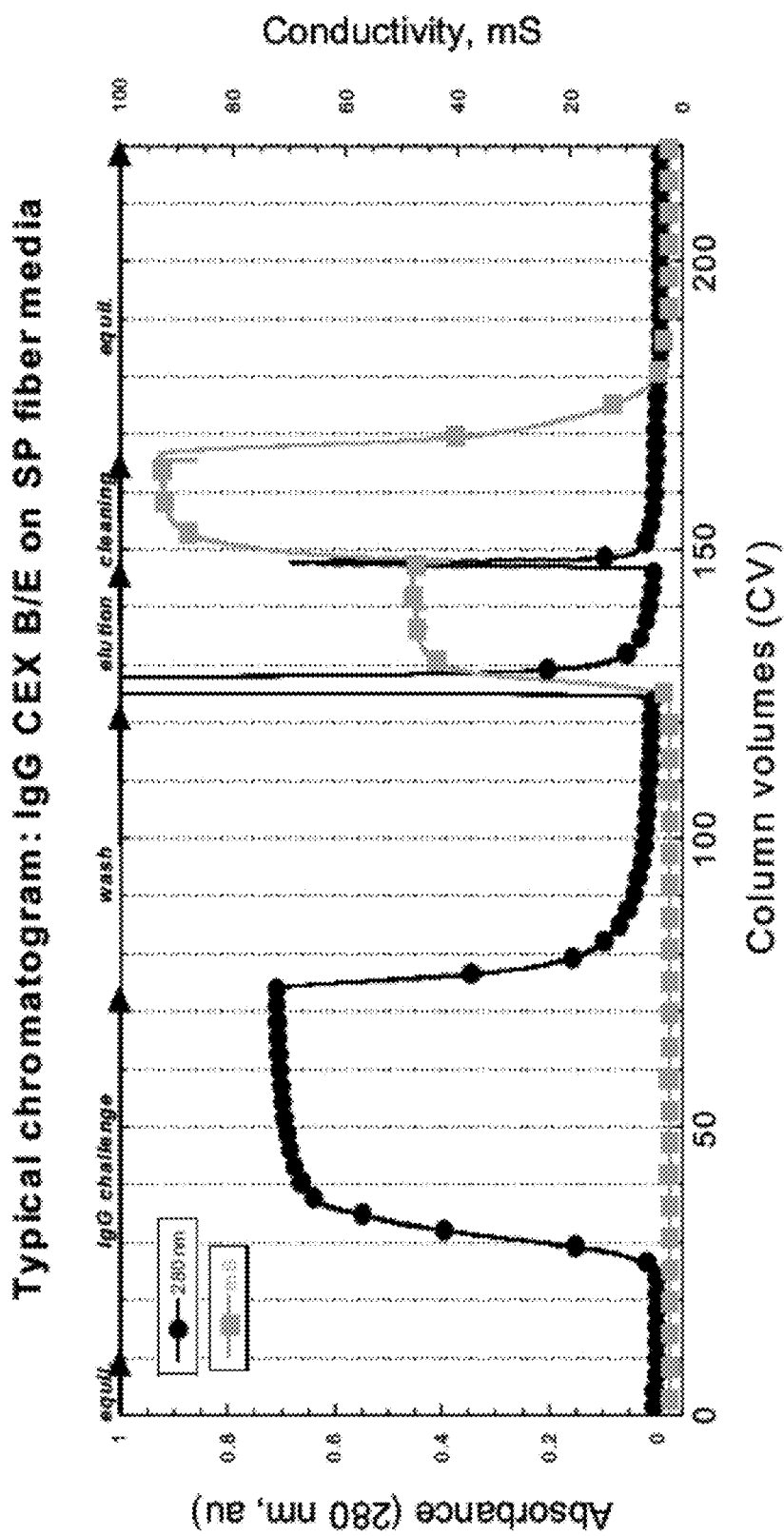
FIG. 2. Typical IgG breakthrough curve and elution peak for the SP-functionalized Allasso winged fiber cation-exchange media (SPFl). Equilibration/wash buffer: 50 mM NaOAc, pH 5; IgG load: 1.73 g/L IgG in 50 mM NaOAc, pH 5; Elution buffer: 0.5 M NaCl in 50 mM NaOAc, pH 5; Cleaning buffer: 0.5 M NaOH.

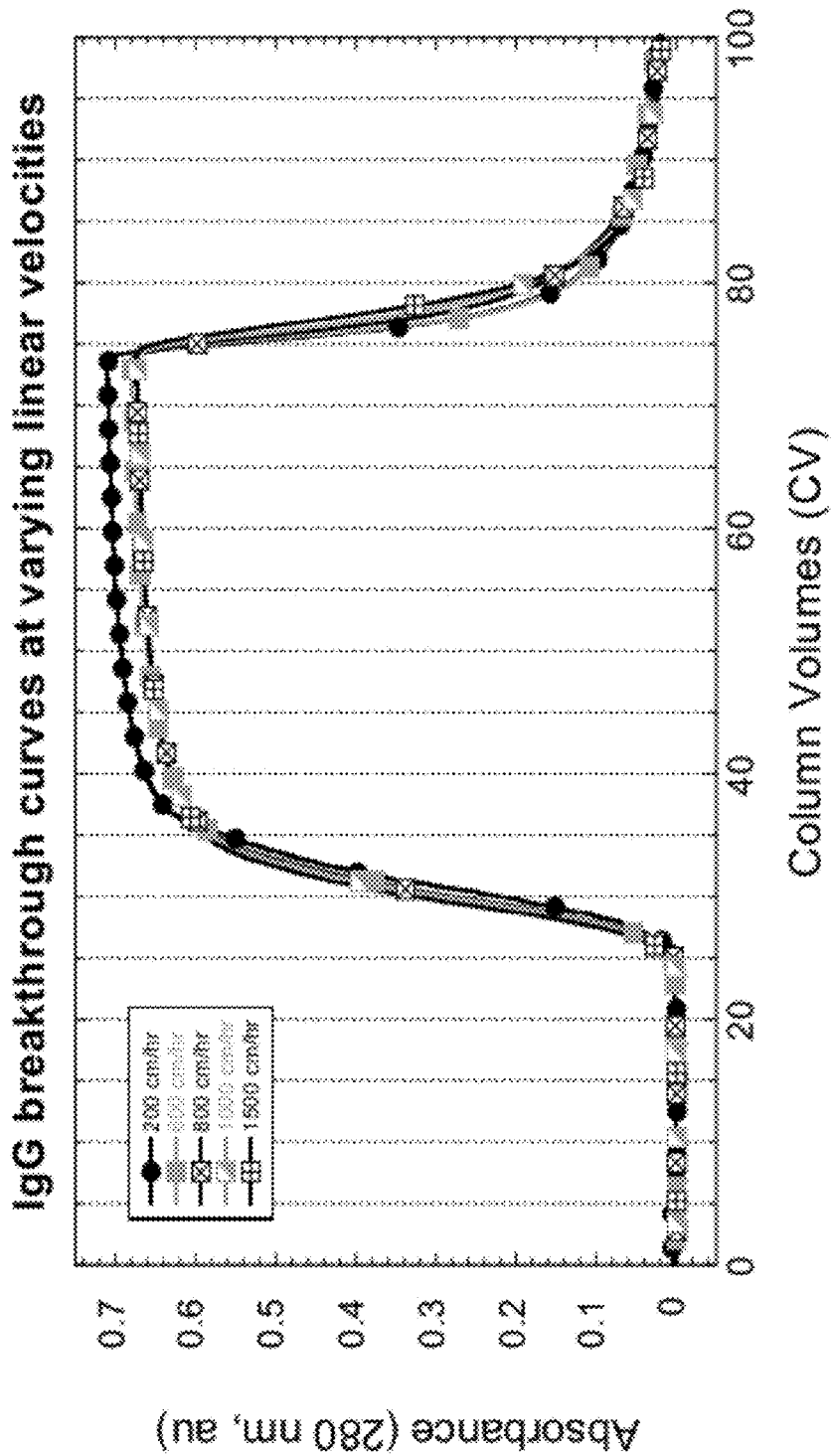
FIG. 3. IgG breakthrough curves for the SP-functionalized Allasso winged fiber cation-exchange media (SPF1) at varying linear velocities.

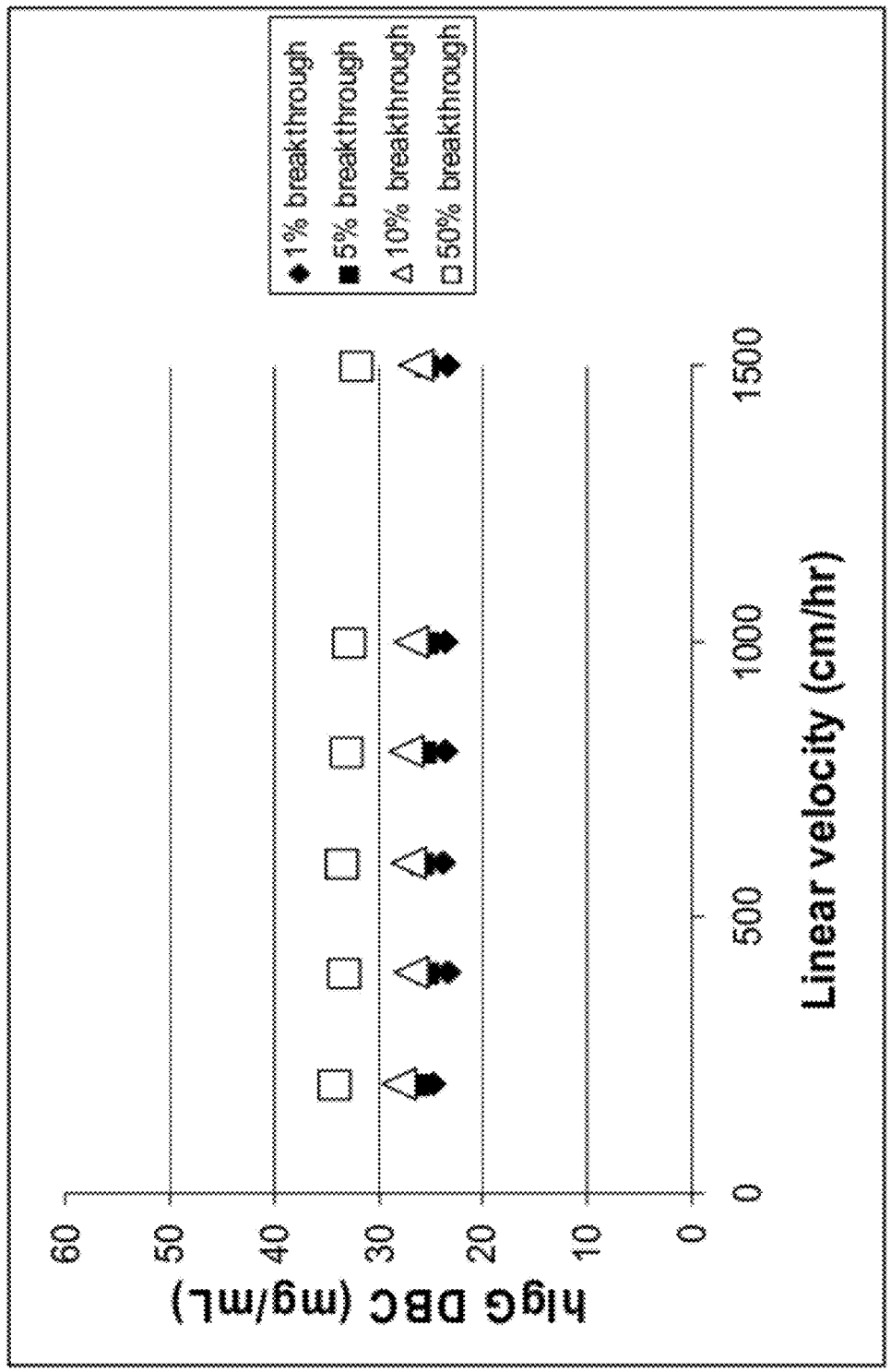
FIG. 4. Plot of IgG DBC for SPF1 at 1, 5, 10, and 50% breakthrough at varying linear velocities.

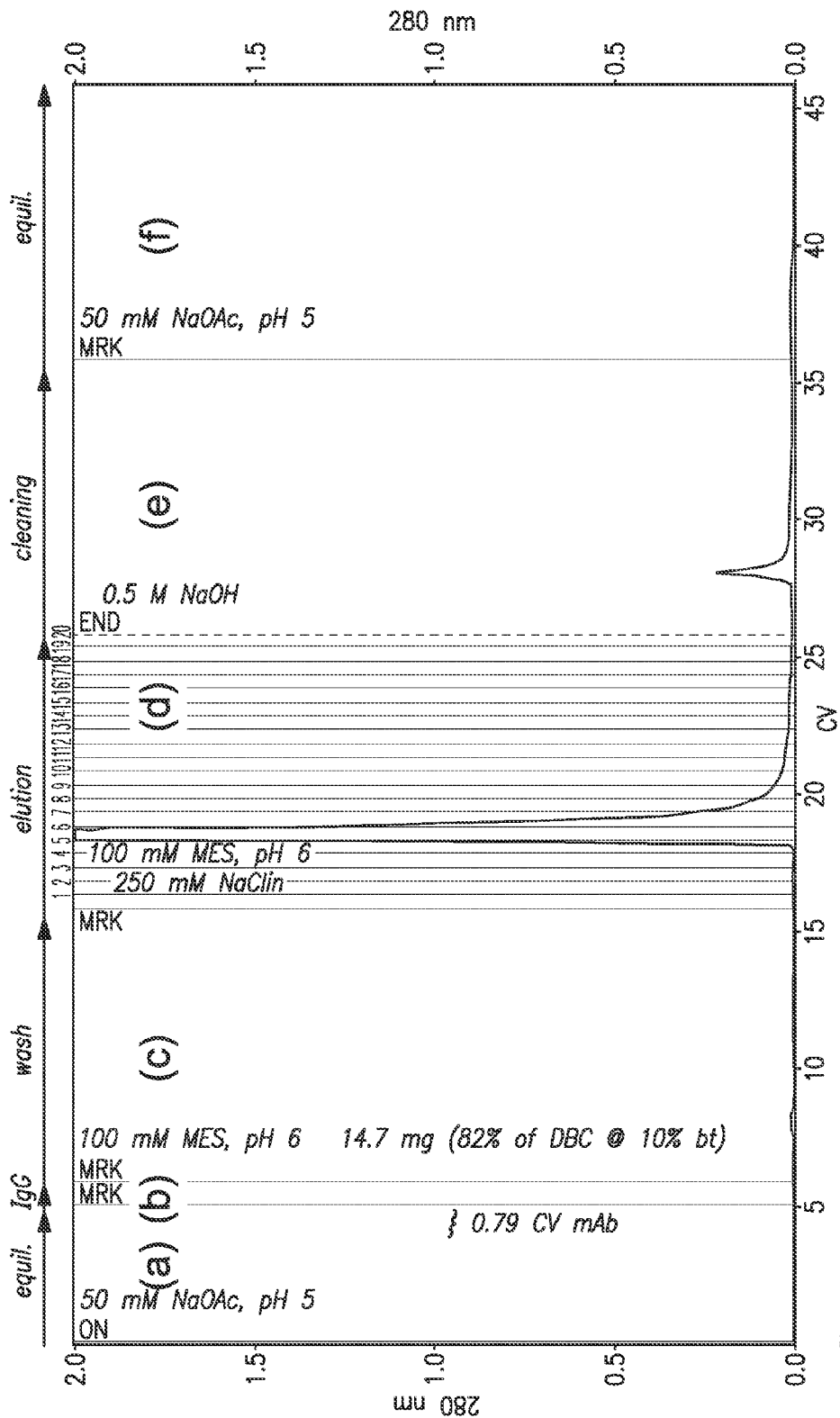

FIG. 5. Chromatogram from a mAb challenge experiment for the SP-functionalized Allasso winged fiber cation-exchange media (SPF1). Process details (a) equilibration buffer, 50 mM sodium acetate, pH 5 (5 CV); (b) sample load, 6.7 g/L mAb challenge solution (Protein A eluate, 0.79 CV); (c) wash buffer, 100 mM MES buffer, pH 6 (10 CV); (d) elution buffer, 250 mM NaCl in 100 mM MES buffer, pH 6 (10 CV, 20 0.5 CV fractions collected); (e) cleaning buffer, 50 mM NaOH (10 CV); (f) equilibration buffer, 50 mM sodium acetate, pH 5 (5 CV)

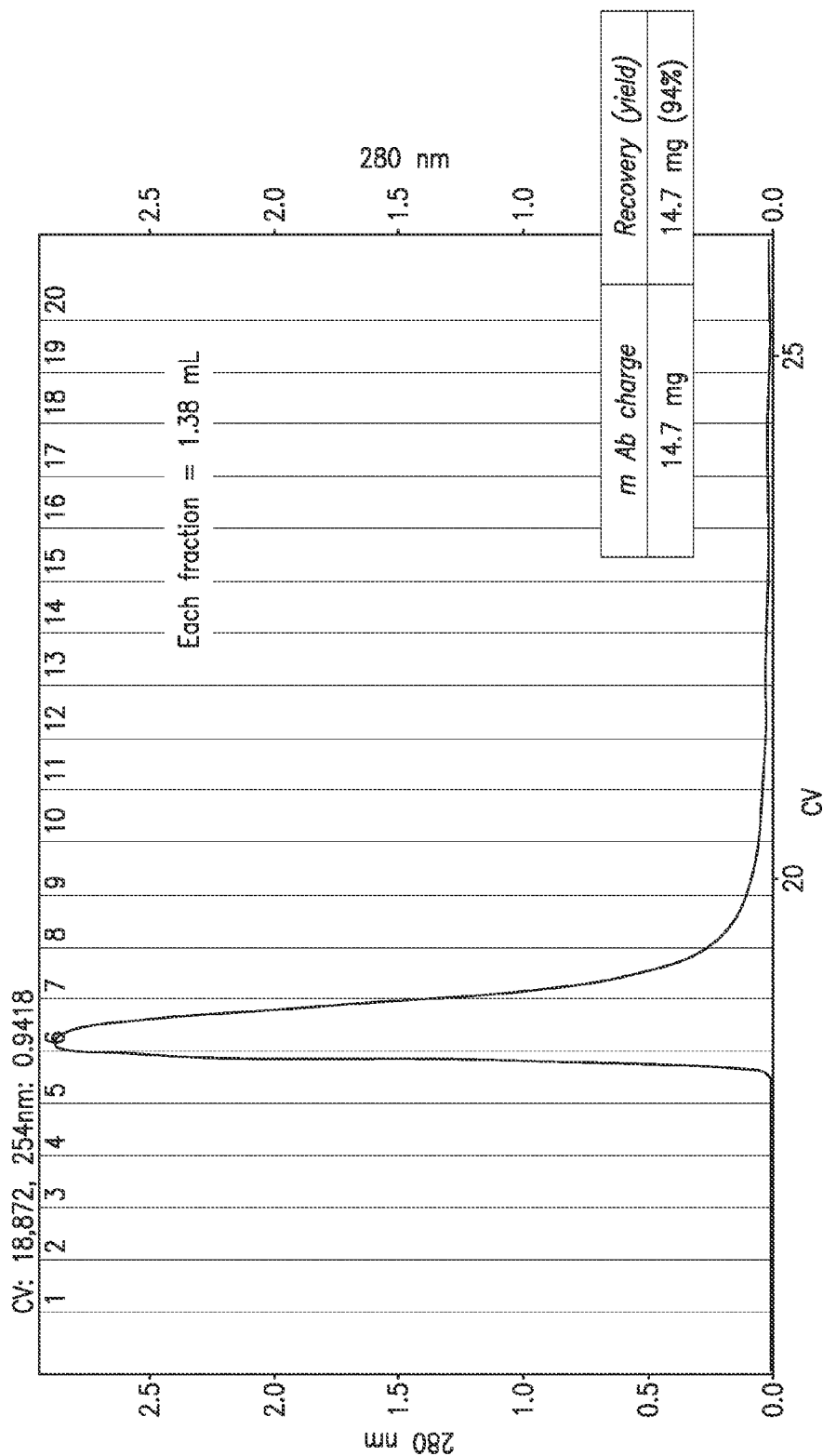
FIG. 6. Typical mAb elution peak for the SP-functionalized Allaso winged fiber cation-exchange media (SPF1). *inset*: Recovery analysis of the elution fractions by measurement of UV absorbance at 280 nm indicates 94% recovery of mAb.

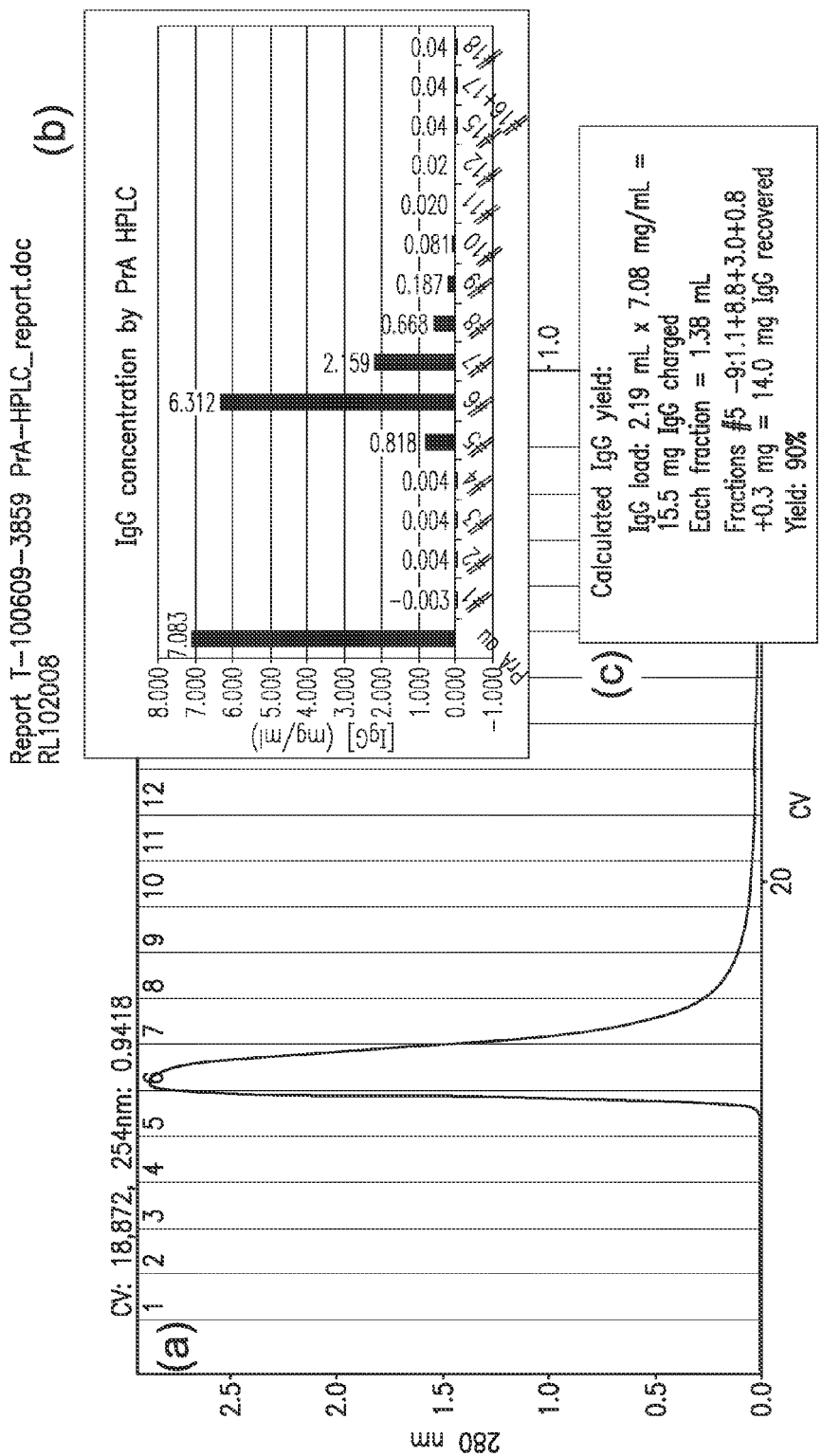

FIG. 7. *IgG quantification by Protein A HPLC* (a) The elution fractions from a mAb challenge experiment using the SP-functionalized Allasso winged fiber cation-exchange media (SPFI). (b) IgG concentration (mg/mL) by protein A HPLC for the elution fractions #1-20. The mAb feed has a IgG concentration of 7.083 mg/mL (first column). (c) Calculation of IgG recovery by analysis of the measured IgG concentrations in elution fractions #5-9.

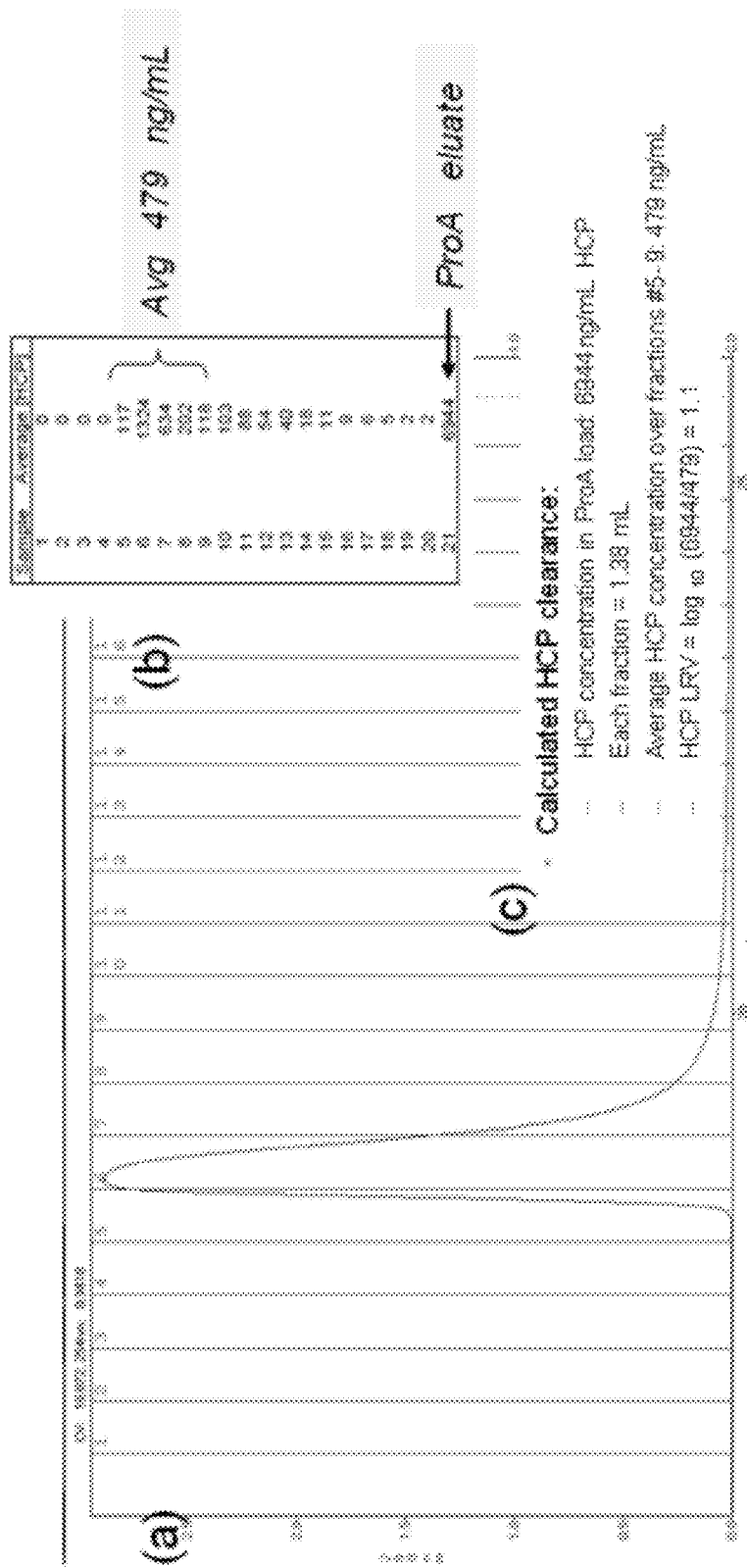

FIG. 8. *CHO-HCP quantification by ELISA.* (a) The elution fractions from a mAb challenge experiment using the SP-functionalized Allasso winged fiber cation-exchange media (SPF1). (b) CHO-HCP concentration (ng/mL) by ELISA for the elution fractions #1-20. The mAb load has an HCP concentration of 6944 ng/mL (line 213). (c) Calculation of HCP clearance (LRV) by analysis of the measured HCP concentrations in elution fractions.

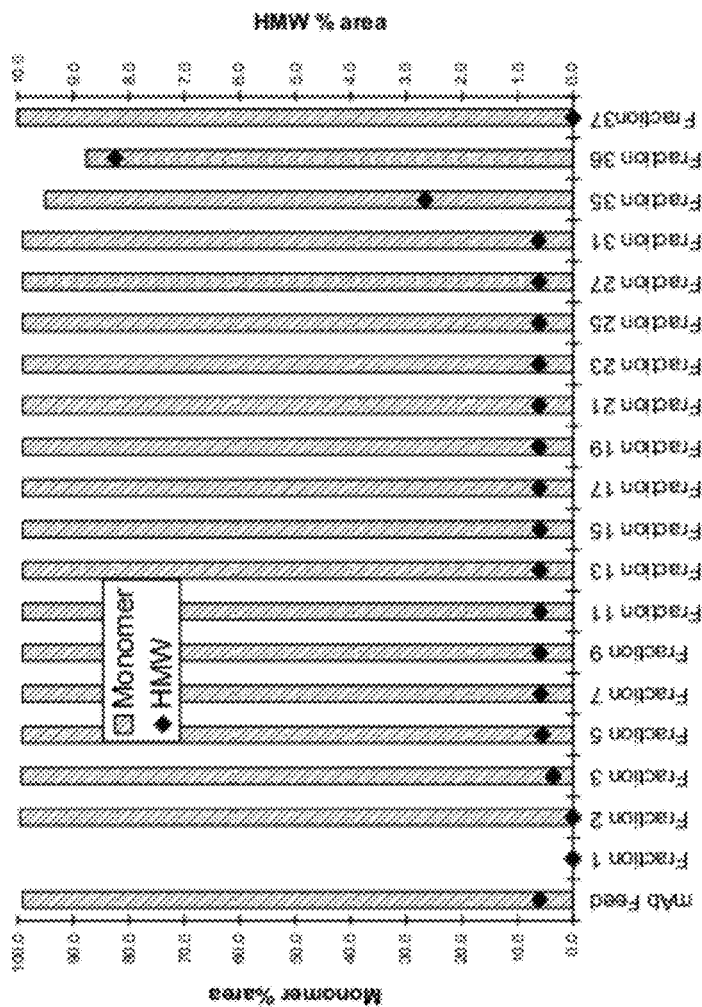

FIG. 9. Flow through aggregate clearance of a monoclonal antibody feed. Evaluation of a flow through aggregate clearance process comprising sulfopropyl-functionalized fiber media in a packed bed format (2.85 mL column volume, 0.33 g/mL packing density). Fractions analyzed by size exclusion chromatography (SEC) to find % monomeric and % HMW aggregated monoclonal antibody compositions for 31 flow through and 3 elution fractions (Fraction #35, 36, 37). Challenge: 6.9 g/L of a monoclonal antibody Protein A elution (pH 5, 19 mS) at a flow rate of 3.2 mL/min (residence time = 54 seconds).

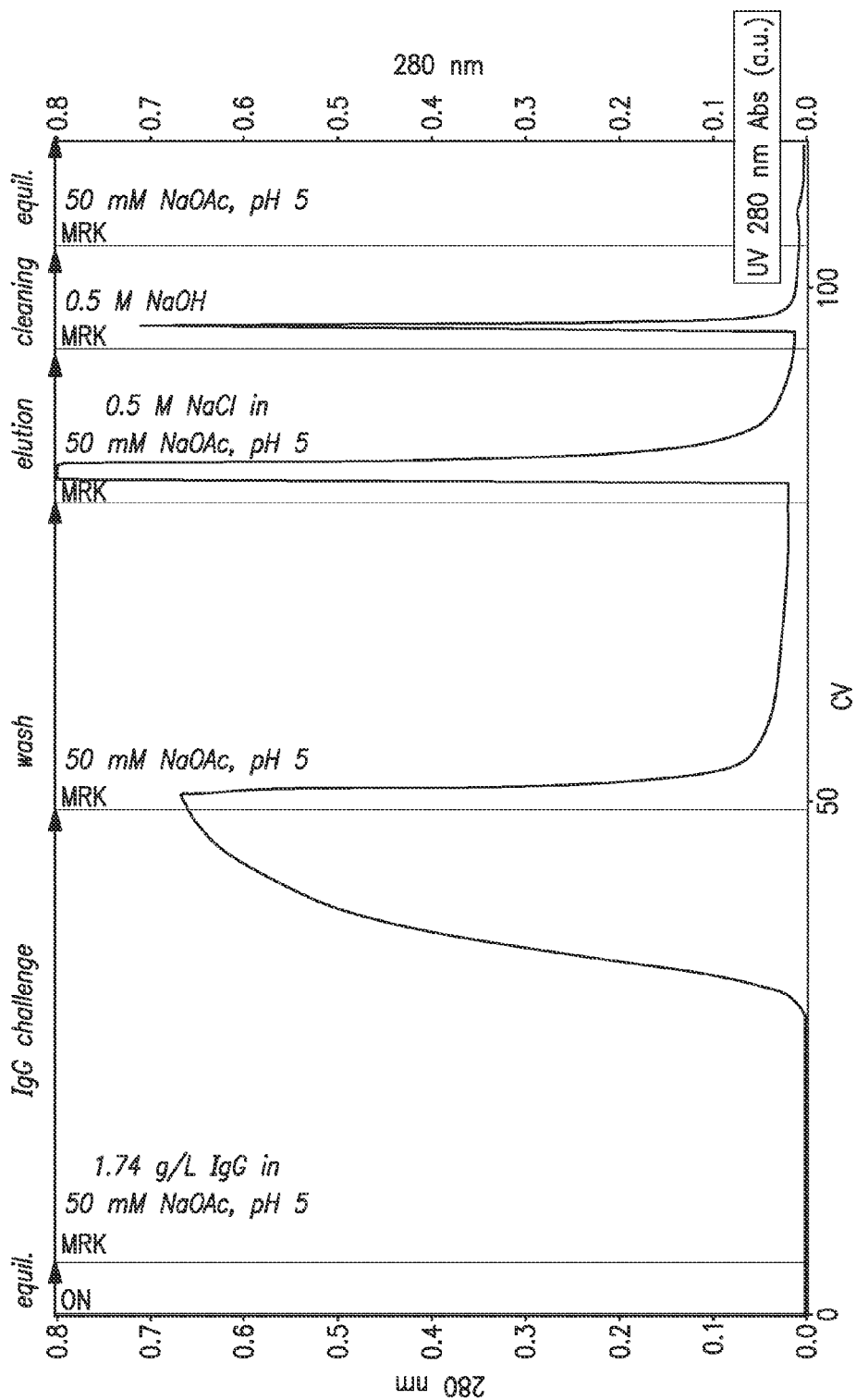
FIG. 10. Typical IgG breakthrough curve and elution peak for the SP-tentacle functionalized Allasso winged fiber cation-exchange media.

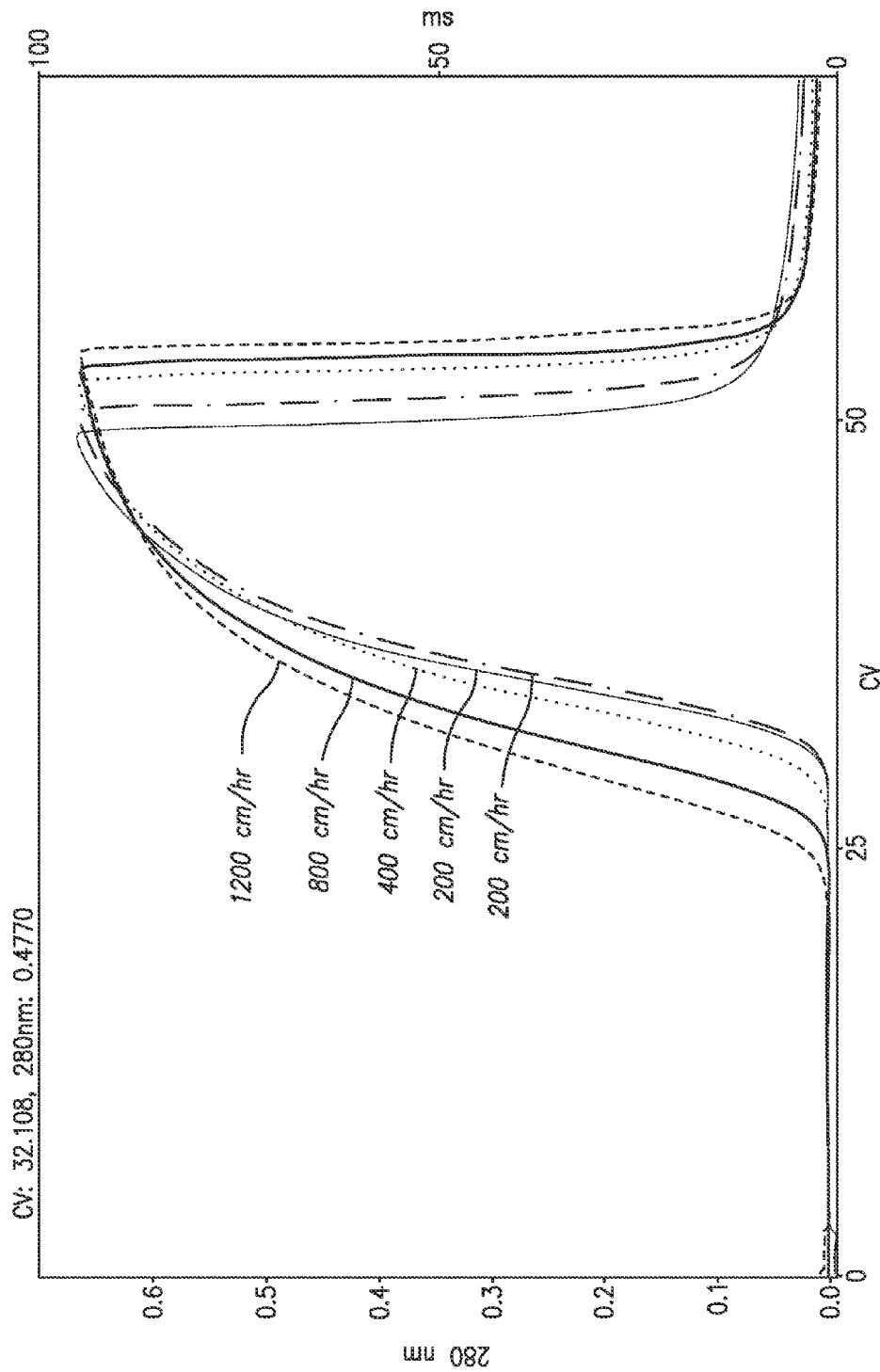
FIG. 11. IgG breakthrough curves for the SP-tentacle functionalized Allasso winged fiber cation-exchange media at varying linear velocities.

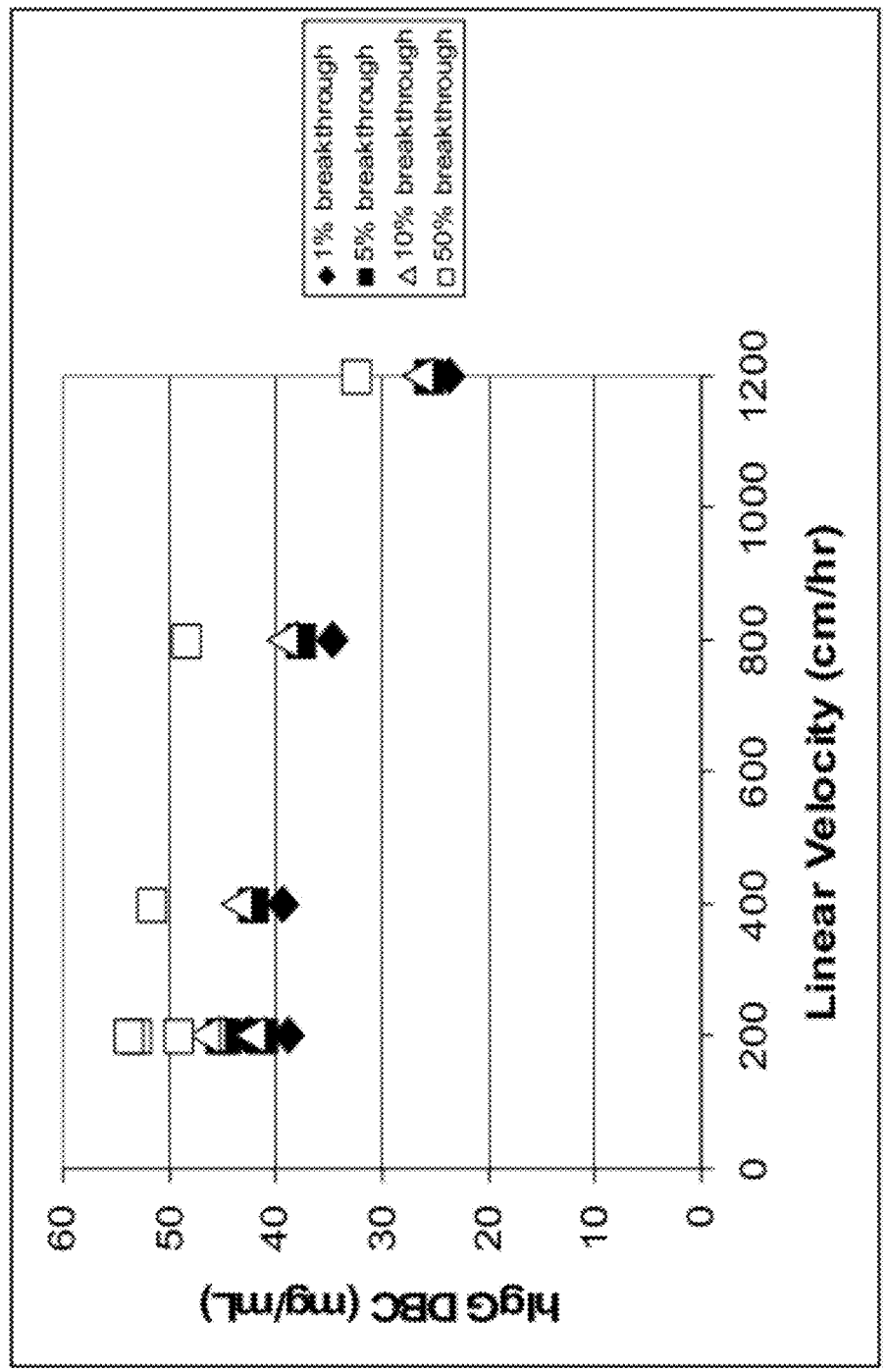
FIG. 12. Plot of IgG DBC for the SP-tentacle functionalized Allasso winged fiber cation-exchange media at 1, 5, 10, and 50% breakthrough at varying linear velocities.

CHROMATOGRAPHY MEDIA AND METHOD

This application claims priority of U.S. Provisional Application Ser. No. 61/369,331 filed Jul. 30, 2010, the disclosure of which is hereby incorporated by reference.

FIELD

The embodiments disclosed herein relate to chromatography media suitable for the purification of biomolecules such as by ion exchange chromatography.

BACKGROUND

The commercial scale purification of various therapeutic biomolecules, such as monoclonal antibodies, is currently accomplished using bead-based chromatography resins. Monoclonal antibodies continue to gain importance as therapeutic and diagnostic agents. The process of screening hybridoma libraries for candidate mABs is both time consuming and labor intensive. Once a hybridoma cell line expressing a suitable mAB is established, a purification methodology must be developed to produce sufficient mAB for further characterization. A traditional method for purifying involves using Protein A or Protein G affinity chromatography, as well as ion exchange chromatography. The purified antibody is desalted and exchanged into a biological buffer using dialysis. The entire process typically requires several days to complete and can be particularly onerous if multiple mABs are to be evaluated in parallel.

Chromatography resins are currently prepared with various ligand structures that enable the beads to function in affinity, cation-exchange, or anion-exchange modes. These resins demonstrate a high porosity and large surface areas that provide materials with sufficient adsorptive capacities for the batch processing of biomolecules at production scales (e.g., 10,000 liters). Chromatography resins typically present a spherical structure that enables an efficient column packing with minimal flow non-uniformities. The interstitial spaces between the beads provide flow channels for convective transport through the chromatography column. This enables chromatography columns to be run with large bed depths at a high linear velocity with a minimal pressure drop. The combination of these factors enables chromatography resins to present the required efficiency, high permeability, and sufficient binding capacity that are required for the large-scale purification of biomolecules. In bead-based chromatography, most of the available surface area for adsorption is internal to the bead. Consequently, the separation process is inherently slow since the rate of mass transport is typically controlled by pore diffusion. To minimize this diffusional resistance and concomitantly maximize dynamic binding capacity, small diameter beads can be employed. However, the use of small diameter beads comes at the price of increased column pressure drop. Consequently, the optimization of preparative chromatographic separations often involves a compromise between efficiency/dynamic capacity (small beads favored) and column pressure drop (large beads favored).

Chromatography media typically has a very high cost (>$1000/L) and significant quantities are required for large scale production columns. As a result, biopharmaceutical manufacturers recycle chromatography resins hundreds of times. Each of these regeneration cycles consumes substantial quantities of media, and each step incurs additional costs associated with the validation of each cleaning, sterilization, and column packing operation.

Several technologies are described in the patent literature and marketed commercially for biopharmaceutical separations based on functionalized fibrous media and/or composites. Most rely on incorporating a porous gel into the fiber matrix, the gel providing the needed surface area to gain reasonable binding capacities. However, in such constructions, poor uniformity in gel location and mass generally leads to poor efficiencies (shallow breakthrough and elution fronts). In addition, resistance to flow can be high even for short bed depths, a problem often aggravated by gel compression under modest pressure loads. Another approach taken has been the incorporation of particulates within the fiber matrix, the particulates often porous and possessing a native adsorptive functionality, examples being activated carbon and silica gel.

It would be desirable to provide the combination of a high surface area fiber with pendant adsorptive functionality for biomolecule chromatography applications, without sacrificing bed permeability and attainable flow rates.

SUMMARY

The shortcomings of the prior art have been addressed by the embodiments disclosed herein, which relate to an adsorptive media for chromatography, particularly ion-exchange chromatography. The chromatography media disclosed is derived from a shaped fiber. In certain embodiments, the shaped fiber presents a fibrillated or ridged structure. These ridges can greatly increase the surface area of the fibers when compared to ordinary fibers. Thus, high surface area is obtained without reducing fiber diameter, which typically results in a significant decrease in bed permeability and a corresponding reduction in flow rate. An example of the high surface area fiber in accordance with certain embodiments is "winged" fibers, commercially available from Allasso Industries, Inc. (Raleigh, N.C.). A cross-sectional SEM image of an Allasso winged fiber is provided in FIG. 1d. These fibers present a surface area of approximately 14 square meters per gram. Also disclosed herein is a method to add surface pendant functional groups that provides cation-exchange or anion-exchange functionality, for example, to the high surface area fibers. This pendant functionality is useful for the ion-exchange chromatographic purification of biomolecules, such as monoclonal antibodies (mAbs).

Embodiments disclosed herein also relate to methods for the isolation, purification or separation of biomolecules with media comprising a high surface area functionalized fiber. These methods can be carried out in a flow through mode or a bind/elute mode. For example, in mAb purification, cation exchange chromatography is typically conducted wherein, operating at a pH below the isoelectric point of the antibody protein and at a modestly depressed solution conductivity, the antibody protein will ionically bind to the support via the ion exchange ligand while unbound contaminants (host cell proteins, nucleic acids, etc.) pass freely through the chromatography bed. These contaminants are further eliminated by flushing the packed bead bed with appropriate buffer solution before releasing the bound mAb product with a buffer of high conductivity sufficient to shield the ionic interaction between bead resin and protein. In contrast, anion exchange chromatography is often used downstream in monoclonal antibody production to further remove residual cell culture contaminants wherein the operation is conducted at solution conditions of pH and conductivity such that the mAb protein will not bind to the cationic surface of the bead resin but instead passes freely through the chromatography column. Proteins and nucleic acids on the other hand that bear a net negative charge will effectively bind to the anion exchange resin and thereby are eliminated from the product.

In accordance with certain embodiments, the media disclosed herein have high bed permeability (e.g., 500-900 mDarcy), low material cost relative to bead-based chromatographic media, 20-60 mg/mL IgG dynamic binding, high separation efficiencies (e.g., HETP<0.1 cm), 50-160 mg/g IgG static binding capacity, and fast convective dominated transport of adsorbate to ligand binding sites.

In accordance with certain embodiments, the use of unique high surface area, extruded fibers (e.g., thermoplastic fibers) allows for high flow permeability (liquid) and uniform flow distribution when configured as a packed bed of randomly oriented cut fibers of lengths between 2-6 mm. Chemical treatment methods to functionalize such fiber surfaces are provided to enable bio-molecular and biological separations based on adsorptive interaction(s). Chemical treatment method can impart a variety of surface chemical functionalities to such fibers based on either ionic, affinity, hydrophobic, etc. interactions or combinations of interactions. The combined economies of fiber production and simple surface chemical treatment processes yield an economical and readily scalable technology for purification operations in biopharmaceutical as well as vaccine production.

In accordance with certain embodiments, an adsorptive separations material is provided that allows for fast processing rates, since mass transport for solutes to and from the fiber surface is largely controlled by fluid convection through the media in contrast to bead-based media where diffusional transport dictates longer contact times and therefore slower processing rates. The ability to capture or remove large biological species such as viruses is provided, which cannot be efficiently separated using conventional bead-based media due to the steric restrictions of bead pores.

BRIEF DESCRIPTION OF THE DRAWINGS

FIG. 1f is another schematic view of functionalization of fibers in accordance with certain embodiments;

FIG. 2 is a IgG breakthrough curve and elution peak for SP-functionalized media in accordance with certain embodiments;

FIG. 3 is a plot of IgG breakthrough curves for SP-functionalized media at varying velocities in accordance with certain embodiments;

FIG. 4 is a plot of IgG dynamic binding capacities at varying linear velocities in accordance with certain embodiments;

FIG. 5 is a chromatogram of a mAb challenge test in accordance with certain embodiments;

FIG. 6 is a mAb elution peak for functionalized media in accordance with certain embodiments;

FIGS. 7a, b and c show IgG quantification by a Protein A HPLC in accordance with certain embodiments;

FIGS. 8a, b and c show ELISA data for CHO-HCP in accordance with certain embodiments;

FIG. 9 is a graph showing flow through aggregate clearance of a monoclonal antibody feed in accordance with certain embodiments;

FIG. 10 is a plot of an IgG breakthrough curve for a SP-tentacle functionalized media in accordance with certain embodiments;

FIG. 11 is a plot of IgG breakthrough curves for SP-tentacle functionalized cation-exchange media at varying velocities in accordance with certain embodiments; and FIG. 12 is a plot of IgG dynamic binding capacities for SP-tentacle functionalized cation exchange media at varying velocities in accordance with certain embodiments.

DETAILED DESCRIPTION

The shaped fiber medium in accordance with the embodiments disclosed herein relies only on the surface of the fiber itself. Since the shaped fiber affords high surface area as well as high permeability to flow, embellishments such as the addition of a hydrogel or porous particulates are not necessary to meet performance objectives with respect to capacity and efficiency. Moreover, without the need to enhance surface area by the addition of a hydrogel or porous particulate, the manufacturing cost of the media described herein is kept to a minimum.

Fibers may be of any length and diameter and are preferably cut or staple fibers or a non-woven fabric. They need not be bonded together as an integrated structure but can serve effectively as individual discrete entities. They may be in the form of a continuous length such as thread or monofilament of indeterminate length or they may be formed into shorter individual fibers such as by chopping fibrous materials (e.g., staple fibers) such as non-woven or woven fabrics, cutting the continuous length fiber into individual pieces, formed by a crystalline growth method and the like. Preferably the fibers are made of a thermoplastic polymer, such as polypropylene, polyester, polyethylene, polyamide, thermoplastic urethanes, copolyesters, or liquid crystalline polymers. Fibers with deniers of from about 1-3 are preferred. In certain embodiments, the fiber has a cross-sectional length of from about 1 µm to about 100 µm and a cross-sectional width of from about 1 µm to about 100 µm. One suitable fiber has a cross-sectional length of about 20 µm and a cross-sectional width of about 10 µm, resulting in a denier of about 1.5. Fibers with surface areas ranging from about 100,000 $cm^2/g$ to about 1,000,000 $cm^2/g$ are suitable. Preferably the fibers have a cross-sectional length of about 10-20 µm.

In certain embodiments, the fibers can readily be packed under compression into a device or container with appropriate ports and dimensions to suit the applications described. The fibers also can be used in a pre-formed bed format such as nonwoven sheetstock material created by a spunbond (continuous filament) or wet-laid (cut fiber) process, common in the nonwovens industry. Suitable pre-formed fiber formats include sheets, mats, webs, monoliths, etc.

Figures 1A, 1B, 1C, 1D:
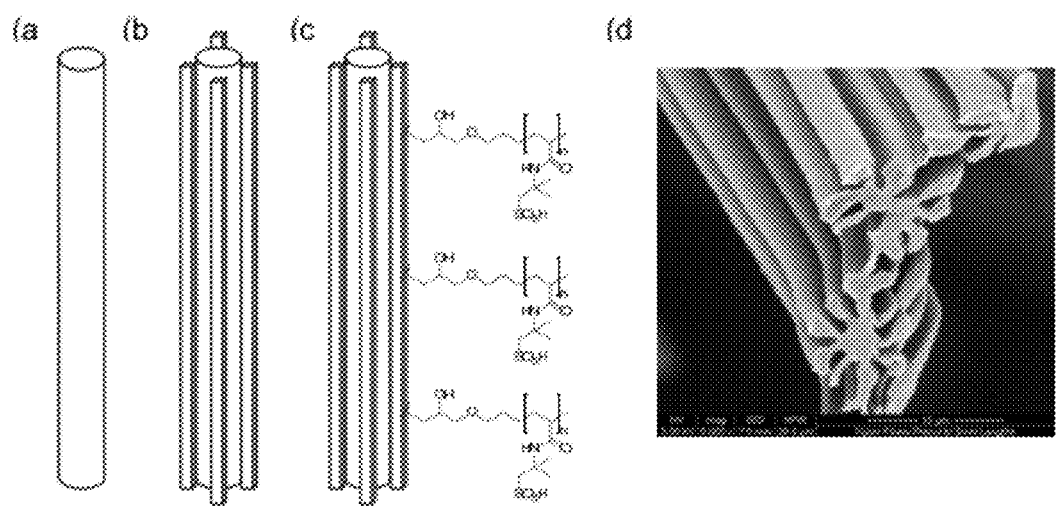
FIG. 1a is a schematic view of a fiber in accordance with the prior art.
FIG. 1b is a schematic view of a ridged fiber that can be used in accordance with certain embodiments.
FIG. 1c is a schematic view of the fiber of FIG. 1b with attached pendant groups in accordance with certain embodiments.
FIG. 1d is an SEM image of a ridged fiber that can be used in accordance with certain embodiments.

In certain embodiments, the fiber cross-section is generally winged-shaped, with a main body region defining a substantially longitudinal axis, and a plurality of projections extending radially outwardly from the main body region. The projections form an array of co-linear channels that extend along the length of the fiber, typically 20-30 such channels per fiber. In certain embodiments, the length of the projections is shorter than the length of the main body region. In certain embodiments, the fiber cross-section is generally winged-shaped, with a middle region comprising a longitudinal axis that runs down the center of the fiber and having a plurality of projections that extend from the middle region (FIG. 1d). In certain embodiments, a plurality of the projections extends generally radially from the middle region. As a result of this configuration, a plurality of channels is defined by the projections. Suitable channel widths between projections range from about 200 to about 1000 nanometers. Suitable fibers are disclosed in U.S. Patent Publication No. 2008/0105612, the disclosure of which is incorporated herein by reference.

Figure 1E:
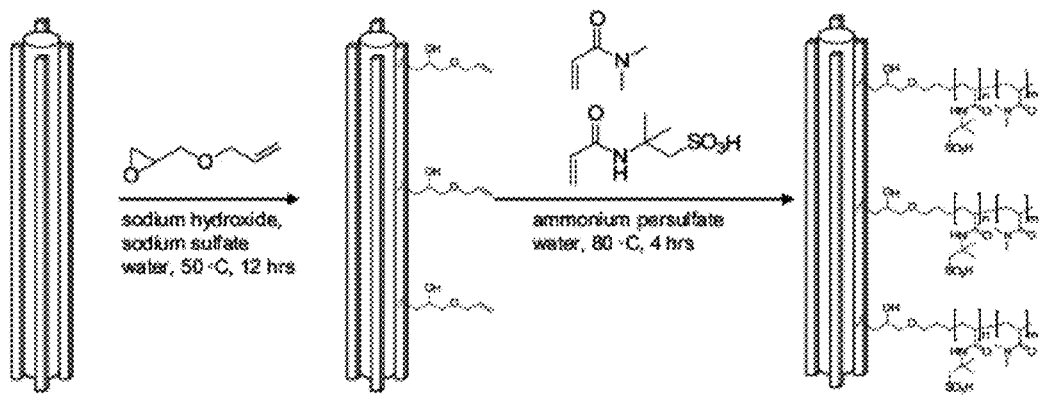
FIG. 1e is a schematic view of functionalization of fibers in accordance with certain embodiments.

The surface functionalization of the high surface area fibers can be accomplished by a two step process. A suitable functionalization process is grafting polymerization, and is illustrated in Scheme 1 shown in FIG. 1e. The functionalization begins with the attachment of pendant allyl groups to the nylon 6 fiber surface by treatment of the fibers with allyl glycidyl ether in the presence of aqueous sodium hydroxide at 50° for 12 hours. The pendant allyl groups serve as anchoring sites on the fiber surface as attachment points for the pendant acrylamide polymer functionality. Conditions for the solution polymerization of acrylamide monomers are provided, and the pendant allyl groups on the fiber surface attach to the growing polymer chains in solution. Thus, the allyl-functionalized fibers are subsequently treated with an aqueous solution of 2-acrylimido-2-methyl-1-propane sulfonic acid, N,N-dimethylacrylimide and ammonium persulfate at 80° C. for 4 hours. Upon heating to 80° C., persulfate decomposition initiates a free radical polymerization of the acrylic monomers. Under these conditions, the pendant allyl groups on the fiber surface serve as attachment points for the pendant acrylic polymer functionality. In this way, the acrylic polymer is covalently attached to the fiber surface.

In certain embodiments, the acrylamide polymer may be prepared separately, and later applied to the nylon fibers as a surface coating. The resulting surface-coated fibers demonstrated comparable IgG binding capacities to the allyl grafted materials.

In accordance with certain embodiments, the functionalization begins with the deposition of a crosslinked coating of hydroxypropylacrylate (HPA) and N,N'-methylenebis(acrylamide) (MBAm) onto the surface of the high surface area fibers, as illustrated in FIG. 1f. This step provides a reactive hydroxylalkyl functionality for a subsequent ceric ion initiated redox polymerization of an acrylamide monomer.

The HPS/MBAm treated fibers are reacted with an aqueous solution of 2-acrylamido-2-methyl-1-propanesulfonic acid sodium salt, ammonium cerium(IV) nitrate, and $HNO_3$ at 35° C. under a nitrogen atmosphere. Under these conditions, cerium oxidation of the crosslinked hydroxylalkyl (hydroxypropylacrylate) functionality on the fiber surface generates free radicals on the fiber surface and initiates a surface grafting polymerization of the 2-acrylamido-2-methyl-1-propanesulfonic acid monomer. Under such conditions, the surface initiated polymerization process produces a polymeric "tentacle" of polymerized (2-acrylamido-2-methyl-1-propanesulfonic acid) monomer. In this way, the acrylamide polymer is covalently attached to the fiber surface. Such processes are known as grafting polymerizations.

A suitable column packing density of between about 0.1-0.4 g/ml, preferably about 0.32 g/ml, at a bed height of 1-5 cm will provide sufficient flow uniformity for acceptable performance in a chromatographic evaluation.

In certain embodiments, the media (functionalized packed fibers) may be delivered to the user in a dry, prepacked format, unlike bead-based media. The fibers can be fused either by thermal or chemical means to form a semi-rigid structure that can be housed in a pressure vessel. By such a construction, the media and accompanying device can be made ready-to-use. Chromatographic bead-based media is generally delivered as loose material (wet) wherein the user is required is load a pressure vessel (column) and by various means create a well-packed bed without voids or channels. Follow-up testing is generally required to ensure uniformity of packing. In contrast, in accordance with certain embodiments, no packing is required by the user as the product arrives ready for service.

The shaped fiber media offers certain advantages over porous chromatographic beads by nature of its morphology. Typically in bead-based chromatography, the rate limiting step in the separation process is penetration of the adsorbate (solute) into the depths of porous beads as controlled by diffusion; for macromolecules such as proteins, this diffusional transport can be relatively slow. For the high surface area fibers disclosed herein, the binding sites are exposed on the exterior of the fibers and therefore easily accessed by adsorbate molecules in the flow stream. The rapid transport offered by this approach allows for short residence time (high flow velocity), thereby enabling rapid cycling of the media by means such as simulated moving bed systems. As speed of processing is a critical parameter in the production of biologics, fiber-based chromatographic media as described herein has particular process advantages over conventional bead-based media.

Conventional chromatographic resins start with porous beads, typically of agarose, synthetic polymer, and silica or glass. These materials are generally of high cost: unfunctionalized agarose beads can cost between $300-$350 per liter and controlled pore glass between $600-$1000 per liter. By contrast, a nonwoven bed of high surface area fibers as described herein in the appropriate densities and thickness to achieve good chromatographic properties are estimated to cost between $20-$50 per liter. This cost advantage will raise the likelihood that this new chromatographic media can be marketed as a "disposable" technology suitably priced for use and disposable after single use or most likely after multiple cycles within one production campaign.

The surface functionalized fiber media of the embodiments disclosed herein (e.g., SP functionalized Allasso fibers, SPF1) demonstrates a high permeability in a packed bed format. Depending on the packing density, the bed permeability can range from >14000 mDarcy to less than 1000 mDarcy. At low packing density of 0.1 g/mL (1 g media/9.3 mL column volume), a bed permeability of 14200 mDarcy at a linear velocity of 900 cm/hr was measured. This value does not change over a wide velocity range (400-1300 cm/hr). Such behavior indicates that the packed fiber bed does not compress at high linear velocity. Subsequent compression of the surface functionalized fiber media (SP functionalized Allasso fibers, SPF1) to a higher packing density of 0.33 g/mL (1 g media/2.85 mL column volume), afforded a bed permeability of 1000 mDarcy at a linear velocity of 900 cm/hr. Likewise, this value of 1000 mDarcy was unchanged over a linear velocity range of 400-1300 cm/hr. Suitable packing densities include between about 0.1 and about 0.5 g/ml.

For a conventional packed-bed, ion exchange chromatography media employed for bioseparations, such as ProRes-S (Millipore Corp, Billerica, Mass.), permeability values of 1900 mDarcy were measured for a packed bed of similar dimensions to the case above (3 cm bed depth, 11 mm ID Vantage column, 2.85 mL column volume). For membrane adsorbers, typical permeability values are in the range of 1-10 mDarcy. For ProRes-S, no significant change in bed permeability was measured over a range of velocities from 400-1300 cm/hr. While this behavior was expected for a semi-rigid bead, such as ProRes-S; a more compressible media (ex. agarose beads) is expected to demonstrate significant decreases in bed permeability at high linear velocities (>200 cm/hr) due to significant compression of the packed bed.

In Table 2, IgG dynamic binding capacity data was presented for the surface functionalized fiber media (SPF1) of embodiments disclosed herein. No significant change in IgG DBC values were measured at 1, 5, 10, 50% breakthrough over a range of linear velocities from 200 cm/hr to 1500 cm/hr and there was no significant change in the shape of the IgG breakthrough curves presented in FIG. 3.

In Table A below, IgG dynamic binding capacity data is presented for ProRes-S that was measured over a wide range of linear velocities. For this traditional, packed bed, bead-based, ion exchange chromatography media (ProRes-S), a linear velocity of 60 cm/hr is recommended to maximize DBC for bind and elute capture chromatography applications. At higher velocities (>60 cm/hr), there is a significant decrease in the IgG dynamic binding capacity. At the highest linear velocity measured (1200 cm/hr) the IgG DBC is only a fraction of that measured for the 60 cm/hr case. A significant broadening of the IgG breakthrough curves were observed when ProRes-S was operated at velocities greater than 60 cm/hr.

For applications that require very short residence times or column operations at linear velocities greater than 60 cm/hr, and especially greater than 200 cm/hr, the SP-functionalized fiber media (SPF1) is better suited for those applications than traditional bead based chromatography resins such as ProRes-S.

TABLE A

IgG DBC values for ProRes-S media at 1, 5, 10, and 50% breakthrough at varying linear velocities.

| | DBC (mg/mL) | | | | | | |
|---|---|---|---|---|---|---|---|
| % Breakthrough | 60 cm/hr | 200 cm/hr | 200 cm/hr | 200 cm/hr | 400 cm/hr | 800 cm/hr | 1200 cm/hr |
| 1 | 49 | 29 | 31 | 22 | 12 | 8 | 6 |
| 5 | 70 | 34 | 36 | 32 | 19 | 11 | 8 |
| 10 | 81 | 38 | 40 | 36 | 21 | 12 | 9 |
| 50 | 103 | 82 | 84 | 80 | 56 | 32 | 23 |

Examples of the high surface area fiber surface functionalization and free radical polymerization grafting procedures are provided below.

Example 1

Surface Modification of High Surface Area Fibers with Pendant Allyl Groups

Nylon Fiber Surface Modification with Allyl Glycidyl Ether.

Into a glass bottle were added allyl glycidyl ether (28.9 g, 250 mmol), sodium sulfate (6.0 g, 42 mmol) and 4 N sodium hydroxide solution (60 mL). 4 g of loose nylon fibers (supplier, lot ID) were added to the mixture. The wet solids were heated to 50° C. for 12 hours.

After cooling to room temperature, the solids were transferred to a Buchner funnel and washed with distilled water (400 mL). The material was allowed to dry under vacuum for 30 minutes.

Obtained 9.4 g as a damp solid.

The material was used immediately in the following step.

Example 2

Free Radical Graft Polymerization of Allyl-Modified, High Surface Area Fibers with Pendant Sulfopropyl Cation-Exchange Functionality Graft Polymerization of Allyl-Modified Nylon (AMPS/DMAM 55/45).

Into a glass bottle were added 2-acrylamido-2-methyl-1-propanesulfonic acid (AMPS, 5.02 g, 24 mmol), N,N-dimethylacrylamide (DMAM, 1.96 g, 20 mmol), ammonium persulfate (0.49 g, 2 mmol) and water (72.8 mL). 9.4 g of loose nylon fibers (Example 1) were added to the mixture. The wet solids were heated to 80° C. for 4 hours.

After cooling to room temperature, the solids were transferred to a Buchner funnel and washed with distilled water (450 mL) and methanol (250 mL). The material was placed in an oven to dry at 70° C. for 12 hrs.

Obtained 4.0 g as a white fibrous solid.

Example 3

Functional Performance of the Resulting Media

The sulfopropyl-functionalized high surface area fibers from Example 2 were evaluated in a cation exchange chromatography application for the purification of a polyclonal human gamma immunoglobulin (IgG). The results of static binding capacity measurements for IgG are provided in Table 1 below. In this study, the static binding capacity of a sample of the unfunctionalized "winged fiber" from Allasso Industries (lot ID 090602PA6C) was compared to samples of sulfopropyl-functionalized fibers prepared by UV-initiated polymerization processes and the thermally initiated polymer grafting process described in Examples 1 and 2 above. The thermally initiated free radical grafting procedure provided a SP-functionalized fiber media with a significantly higher static binding capacity (50-80 mg IgG/g fiber sample) than that of the UV-initiated process (10-30 mg IgG/g fiber sample) and the unfunctionalized fibers alone (20 mg IgG/g fiber sample). IgG elution studies with 1 M NaCl solution were also performed on these samples. 50-70% recovery of the bound IgG from the SP-functionalized material under these elution conditions was measured. Based on these results, the SP-functionalized fiber media demonstrates sufficient static binding capacity and salt elution properties for functional performance testing in a biomolecule chromatography application.

TABLE 1

Static binding capacity measurement. Challenge: 2 g/L polyclonal human IgG (SeraCare LifeSciences, Milford, MA) in 50 mM Sodium Acetate (pH 5). Wash buffer 50 mM Sodium Acetate (pH 5). Elution buffer 1M sodium chloride in 50 mM Sodium Acetate (pH 5).

| Sample ID | Process | Amt (g) | IgG bound (mg) | SBC (mg/g) | IgG eluted (mg) | % recovery |
|---|---|---|---|---|---|---|
| unfunctionalized Allasso | — | 0.1 g | 1.8 | 18 | 0.7 | 41% |
| unfunctionalized Allasso | — | 0.1 g | 2.1 | 21 | 0.2 | 10% |
| SP-funct. Allasso | UV | 0.1 g | 2.7 | 27 | 2.3 | 85% |
| SP-funct. Allasso | UV | 0.1 g | 1.2 | 12 | 2.3 | 190% |
| SP-funct. Allasso (Example 2) | graft | 0.1 g | 7.9 | 79 | 3.8 | 47% |
| SP-funct. Allasso (Example 2) | graft | 0.1 g | 7.0 | 70 | 3.3 | 47% |
| SP-funct. Allasso (Example 2) | graft | 0.1 g | 6.2 | 53 | 4.3 | 69% |
| SP-funct. Allasso (Example 2) | graft | 0.1 g | 5.6 | 48 | 2.6 | 46% |

Example 4

Approximately 0.3 g of loose SP-functionalized Allasso winged fibers were loaded into a 6.6 mm ID Omnifit chromatography column. The bed volume was adjusted to 2 cm by compression of the top solvent distribution header to give a column volume of 0.68 mL. IgG dynamic binding capacity measurements were performed according to the following procedure:
10 CV 50 mM NaOAc buffer (pH 5) (equilibration)
60 CV 2 mg/mL IgG (SeraCare) in 50 mM NaOAc buffer (pH 5) (IgG Challenge)
80 CV 50 mM NaOAc buffer (pH 5) (wash)
50 CV 1 µM NaCl in 50 mM NaOAc buffer (pH 5) (elution)
20 CV 0.5 M NaOH (cleaning)
60 CV 50 mM NaOAc buffer (pH 5) (wash)

FIG. 2 provides an example of a typical IgG breakthrough curve for the SPF1 fibers described in example 2 in accordance with certain embodiments. There is a sharp breakthrough curve and IgG dynamic binding capacities were measured ranging between 20 and 30 mg/mL (Table 2). Quantitative recovery of the bound IgG upon elution with 1 M sodium chloride in 50 mM NaOAc buffer (pH 5) was achieved.

TABLE 2

IgG DBC values for the SP functionalized media of example 2 (SPF1) at 1, 5, 10, and 50% breakthrough at varying linear velocities.

| | DBC (mg/mL) | | | | | |
|---|---|---|---|---|---|---|
| % Breakthrough | 200 cm/hr | 400 cm/hr | 600 cm/hr | 800 cm/hr | 1000 cm/hr | 1500 cm/hr |
| 1 | 25 | 23 | 24 | 24 | 24 | 23 |
| 5 | 26 | 25 | 26 | 25 | 25 | 25 |
| 10 | 28 | 27 | 27 | 27 | 27 | 26 |
| 50 | 34 | 33 | 33 | 33 | 33 | 32 |

FIG. 3 provides overlaid IgG breakthrough curves for the SPF1 fiber media column at varying linear velocities, ranging from 200 cm/hr to 1500 cm/hr. There is no change in the shape of the breakthrough curve as linear flow velocity is increased.

FIG. 4 shows minimal change in the measured IgG dynamic binding capacity even at very high velocities (1500 cm/hr). This behavior is indicative of a system that is dominated by convective transport of IgG molecules to the ionic ligand binding site.

In contrast, traditional bead-based ion-exchange chromatography resins will show a significant decrease in dynamic binding capacity and more diffuse breakthrough curves as velocities are increased. At very high velocities, bed compression may compromise the integrity of the beads, resulting in poorer flow uniformity and decreased chromatographic performance.

Example 5

Nylon Surface Modification with Acrylamide Copolymer Coating

Solution Polymerization of AMPS/DMAM 55/45.

Into a 250 mL three-necked roundbottom flask were added 2-acrylamido-2-methyl-1-propanesulfonic acid (AMPS, 10.04 g, 48 mmol), N,N-dimethylacrylamide (DMAM, 3.92 g, 40 mmol), ammonium persulfate (0.98 g, 4 mmol) and water (146 mL). The solution was heated to 80° C. for 4 hours. After cooling to room temperature, the polymer solution was used immediately in the following step.

Nylon Fiber Surface Modification with AMPS/DMAM Polymer Coating.

Into a glass bottle were added 19 g of AMPS/DMAM 55/45 copolymer solution prepared above and 1 g of loose nylon fibers (Allasso Industries, #090602PA6C). The wet solids were heated at 80° C. for 24 hours. After cooling to room temperature, the solids were transferred to a Buchner funnel and washed with distilled water (3×50 mL) and methanol (1×50 mL). The material was allowed to dry under vacuum for 10 minutes. The material was placed in an oven to dry at 40° C. for 24 hrs.

Obtained 0.9 g as a white fibrous solid.

Static Binding Capacity Measurement.

The results of static binding capacity measurements for IgG are provided in Table 3 below. In this study, the static binding capacity of a sample of the unfunctionalized "winged fiber" from Allasso (lot ID 090602PA6C) was compared to a sample of the sulfopropyl-functionalized fibers prepared by the solution polymer coating process of this example (Example 5). In this study, the solution polymer coating procedure provided a SP-functionalized fiber media with a higher static binding capacity (30-40 mg IgG/g fiber sample) than that of the unfunctionalized fibers alone (1 mg IgG/g fiber sample). Based on these results, the SP-functional polymer fiber coating can be installed by simple coating and thermal annealing of an AMPS/DMAM copolymer solution.

TABLE 3

Static binding capacity measurement. Challenge: 2 g/L polyclonal human IgG (SeraCare LifeSciences, Milford, MA) in 50 mM Sodium Acetate (pH 5).

| Sample ID | Process | Amt (g) | IgG bound (mg) | SBC (mg/g) |
|---|---|---|---|---|
| unfunctionalized Allasso #090602PA6C | — | 0.1 g | 0.1 | 1 |
| SP-funct. Allasso (Example 5) | coating | 0.1 g | 4.8 | 42 |
| SP-funct. Allasso (Example 5) | coating | 0.1 g | 3.4 | 32 |

Example 6

Surface Modification of High Surface Area Fibers with Pendant Allyl Groups

Nylon Fiber Surface Modification with Allyl Glycidyl Ether.

Into a 0.5 L flask were added allyl glycidyl ether (70.7 g, 620 mmol), sodium sulfate (14.9 g, 105 mmol) and 4 N sodium hydroxide solution (350 mL). 10 g of loose nylon fibers (Allasso Industries, #090602PA6C) were added to the mixture. The wet solids were heated to 50° C. for 12 hours. After cooling to room temperature, the solids were transferred to a Buchner funnel and washed with distilled water (1.5 L) and methanol (0.5 L). The material was allowed to dry under vacuum for 30 minutes. The material was placed in an oven to dry at 50° C. for 18 hrs.

Obtained 8.8 g as a white fibrous solid.

Example 7

Free Radical Graft Polymerization of Allyl-Modified, High Surface Area Fibers with Pendant Sulfopropyl Cation-Exchange Functionality Graft Polymerization of Allyl-Modified Nylon (AMPS/DMAM 55/45).

Into glass vials were added 2-acrylamido-2-methyl-1-propanesulfonic acid (AMPS), N,N-dimethylacrylamide (DMAM), ammonium persulfate and water according to the ratios provided in Table 4 below. Loose allyl glycidyl ether-modified nylon fibers (Example 6) were added to each mixture. The wet solids were heated to 80° C. for 4 hours. After cooling to room temperature, the wet solids were each transferred to a Buchner funnel and washed with distilled water (3×50 mL) and methanol (1×50 mL). The material was placed in an oven to dry at 40° C. for 12 hrs.

The dried, surface-modified fiber samples are ready for static binding capacity measurements with an IgG challenge solution.

Static Binding Capacity Measurement.

The results of static binding capacity measurements for IgG are also provided in Table 4 below. In this study, the static binding capacity of a sample of the unfunctionalized "winged fiber" from Allasso (lot ID 090602PA6C) was compared to the samples of the sulfopropyl-functionalized fibers prepared by the thermally initiated polymer grafting process (samples A-G). In this study, the IgG static binding capacity of the SP-functionalized fiber media can be influenced by the AMPS/DMAM polymer composition and the concentration of the reaction solution. For example, samples E and G present IgG static binding capacities that are substantially higher than those of the unfunctionalized nylon fibers alone (6 mg IgG/g fiber sample) as well as the A and C samples that were prepared with a higher AMPS content.

slurry was allowed to agitate overnight. The fiber slurry was transferred into an 11 mm ID vantage column, using a vacuum to draw excess liquid through the column and to facilitate the compression of the staple fibers. After the slurry was transferred to the column, the top header of the column was installed, and the header compressed to give a final column volume of 2.76 mL (bed compression to target performance). HETP and peak asymmetry measurements were performed using a 2 wt % acetone solution. HETP was measured to be less than 0.1 cm and peak asymmetry was measured to be less than 2.0.

mAb Purification by Cation Exchange Chromatography.

In FIGS. 5 and 6, an example is provided of a chromatogram from a bind/elute purification of a mAb using the cation exchange media of Example 2. In this example, 0.79 CV (2.18 mL) of a protein A elution containing 6.7 mg/mL mAb (14.7 mg mAb) were applied to the column and eluted with 250 mM NaCl in 100 mM MES buffer (pH 6). The mAb elution peak was collected in 20 0.5 CV fractions (each fraction=1.38 mL). Quantification of the mAb elution fractions by measurement of the UV absorbance of each fraction at 280 nm afforded a recovery of 13.8 mg (94% yield). The IgG elution fractions were also analyzed by protein A HPLC in FIG. 7. This analysis also provides the IgG concentration of each elution fraction. By this analysis, the mAb elution is primarily in fractions #5-9, and the mAb recovery is 90%.

TABLE 4

Graft polymerization compositions and IgG static binding capacity measurement data. Challenge: 2 g/L polyclonal human IgG (SeraCare LifeSciences, Milford, MA) in 50 mM Sodium Acetate (pH 5).

| Sample ID | Process | Fiber Amount (g) | AMPS (g, mol) | DMAM (g, mol) | ammonium persulfate (g, mol) | water (mL) | Product (g) | avg. IgG SBC (mg/g) |
|---|---|---|---|---|---|---|---|---|
| A | graft | 0.5 g | 0.9 g, 4 mmol | 0.1 g, 1 mmol | 0.2 g, 1 mmol | 9 mL | 0.5 g | 13 |
| B | graft | 0.5 g | 0.9 g, 4 mmol | 0.1 g, 1 mmol | 0.1 g, 0.5 mmol | 4 mL | did not isolate | — |
| C | graft | 0.5 g | 0.9 g, 4 mmol | 0.2 g, 2 mmol | 0.2 g, 1 mmol | 19 mL | 0.5 g | 6 |
| D | graft | 0.5 g | 0.3 g, 1 mmol | 0.4 g, 4 mmol | 0.1 g, 0.5 mmol | 6 mL | did not isolate | — |
| E | graft | 0.5 g | 0.3 g, 1 mmol | 0.4 g, 4 mmol | 0.1 g, 0.5 mmol | 3 mL | 1.3 g | 114 |
| F | graft | 0.5 g | 0.3 g, 1 mmol | 0.4 g, 4 mmol | 0.3 g, 1 mmol | 13 mL | did not isolate | — |
| G | graft | 0.5 g | 0.6 g, 3 mmol | 0.3 g, 2 mmol | 0.1 g, 0.5 mmol | 9 mL | 0.5 g | 150 |
| Allasso #090602PA6C | — | — | — | — | — | — | — | 6 |

Functional Performance of the Media.

The performance of the sulfopropyl-functionalized high surface area fibers from Example 2 was evaluated in the following Example for the bind and elute purification of a monoclonal antibody (mAb) by cation exchange chromatography. The mAb was provided as an eluate from a protein A column at a concentration of 6.7 mg/mL.

Example 8

Bind and Elute Purification of Monoclonal Antibodies

Column Packing.

0.9 g of the sulfopropyl-functionalized high surface area fibers from Example 2 were slurried in 100 g isopropanol for 30 minutes. 400 mL of deionized water was added and the In FIG. 8, ELISA data is provided for the Chinese hamster ovary-host cell protein concentration (CHO-HCP) of each mAb elution fraction. The HCP is primarily eluted in fractions #5-9, with an average concentration of 479 ng/mL. Since the mAb challenge solution had a HCP concentration of 6944 ng/mL, a HCP clearance log reduction value (LRV) of 1.1 was calculated.

Example 9

Surface Modification of High Surface Area Fibers with Pendant Allyl Groups

Nylon Fiber Surface Modification with Allyl Glycidyl Ether.

Into a glass vial were added allyl glycidyl ether (28.8 g, 252 mmol), sodium sulfate (6.0 g, 43 mmol) and 4 N sodium hydroxide solution (60 mL). 4 g of loose nylon fibers (Allasso Industries, #090602PA6C) were added to the mixture. The wet solids were heated to 50° C. for 12 hours.

After cooling to room temperature, the solids were transferred to a Buchner funnel and washed with distilled water (0.5 L). The material was allowed to dry under vacuum for 30 minutes. The damp material was used immediately in the following step.

Example 10

Free Radical Graft Polymerization of Allyl-Modified, High Surface Area Fibers with a Pendant Trimethylammonium Anion-Exchange Functionality Graft Polymerization of Allyl-Modified Nylon (APTAC 100).

Into a glass vial were added (3-Acrylamidopropyl)trimethylammonium chloride (APTAC, 9.1 g, 44 mmol), ammonium persulfate (0.64 g, 3 mmol), water (27 mL) and 10 g of the wet allyl glycidyl ether modified fibers from example 9 above. The solution was heated to 80° C. for 4 hours.

After cooling to room temperature, the wet solids were each transferred to a Buchner funnel and washed with distilled water (100 mL) and methanol (30 mL). The material was allowed to dry under vacuum for 120 minutes. The material was placed in an oven to dry at 50° C. for 12 hrs.

Obtained 6.1 g as a light yellow, fibrous solid.

The dried, surface-modified fiber samples are ready for static binding capacity measurements with a bovine serum albumin (BSA) challenge solution.

Example 11

Static Binding Capacity Measurement.

In order to test the performance of the trimethylammonium-functionalized fibers in an anion-exchange application, BSA static binding capacity measurements were performed. The results of static binding capacity measurements for BSA are provided in Table 5 below. In this study, the static binding capacity of a sample of the trimethylammonium-functionalized fibers prepared by the thermally initiated polymer grafting process of Example 10 was recorded. The BSA static binding capacity of the trimethylammonium-functionalized fiber media from Example 10 is between 1 and 19 mg/g.

TABLE 5

Static binding capacity measurement. Challenge: 0.5 g/L bovine serum albumin (BSA) in 25 mM TRIS buffer (pH 8).

| Sample ID | Process | Amt (g) | BSA bound (mg) | SBC (mg/g) |
| --- | --- | --- | --- | --- |
| Q-funct. fiber example 10 | graft | 0.1 g | 0.1 | 1 |
| Q-funct. fiber example 10 | graft | 0.1 g | 2.0 | 19 |

Example 12

Graft Polymerization of Un-Modified Nylon Fibers.

Into 6×200 mL bottles were added 3-sulfopropylmethacrylate potassium salt (3-SPMA), water, nylon fibers (Allasso Industries) and 1 M $HNO_3$ solution (in the amounts described in the table below). A 0.4 M solution of ammonium cerium (IV) nitrate (CAN) in 1 M $HNO_3$ were added to each bottle. The reaction bottles were capped and the mixtures were heated to 35° C. for 18 hours.

After cooling to room temperature, the fiber solids from each bottle were washed with a solution of 0.2 M ascorbic acid in 0.5 M sulfuric acid (3×50 mL), DI water (3×50 mL), 1 M sodium hydroxide solution (3×50 mL), DI water (3×50 mL) and acetone (1×50 mL). The material was placed in an oven to dry at 40° C. for 12 hrs.

Obtained samples of a white fibrous solid (see Table 6 for recovery and weight add-on data).

TABLE 6

Cerium redox graft polymerization compositions and recovery data.

| Reaction # | Allasso fiber (g) | 3-SPMA monomer, g (mmol) | CAN (mM) | $HNO_3$ (mM) | water (mL) | Product wt, g (% add-on) |
| --- | --- | --- | --- | --- | --- | --- |
| Example 12-1 | 1.5 g | 7.39 g (30 mmol) | 8 mM | 240 mM | 55.5 mL | 1.72 g, (+15%) |
| Example 12-2 | 1.5 g | 9.24 g (38 mmol) | 6 mM | 180 mM | 60.4 mL | 1.64 g (+9%) |
| Example 12-3 | 1.5 g | 7.39 g (30 mmol) | 4 mM | 120 mM | 65.3 mL | 1.54 g (+3%) |
| Example 12-4 | 1.5 g | 5.54 g (23 mmol) | 6 mM | 180 mM | 60.4 mL | 1.74 g (+16%) |
| Example 12-5 | 1.5 g | 7.39 g (30 mmol) | 8 mM | 80 mM | 67.5 mL | 1.56 g (+4%) |
| Example 12-6 | 1.5 g | 9.24 g (38 mmol) | 6 mM | 60 mM | 69.4 mL | 1.52 g (+1%) |

Static Binding Capacity Measurement.

The results of static binding capacity measurements for IgG are provided in Table 7 below. The SP-functionalized tentacle fiber media demonstrates IgG static binding capacities comparable to bead-based cation-exchange media employed in commercial biomolecule chromatography applications.

TABLE 7

Static binding capacity measurement. Challenge: 2 g/L polyclonal human IgG (SeraCare Life Sciences, Milford, MA) in 50 mM Sodium Acetate (pH 5).

| Sample | Amt (g) | IgG Bound (mg) | SBC (mg/g) | SBC (mg/mL)[1] |
| --- | --- | --- | --- | --- |
| Example 12-1 | 0.111 | 14.6 | 131 | 43 |
| Example 12-2 | 0.102 | 16.4 | 160 | 52 |
| Example 12-3 | 0.104 | 10.9 | 105 | 34 |

TABLE 7-continued

Static binding capacity measurement. Challenge: 2 g/L polyclonal human IgG (SeraCare Life Sciences, Milford, MA) in 50 mM Sodium Acetate (pH 5).

| Sample | Amt (g) | IgG Bound (mg) | SBC (mg/g) | SBC (mg/mL)[1] |
|---|---|---|---|---|
| Example 12-4 | 0.100 | 14.9 | 149 | 49 |
| Example 12-5 | 0.108 | 12.6 | 116 | 38 |
| Example 12-6 | 0.103 | 14.2 | 138 | 45 |

[1]Based on a 0.33 g/mL fiber packing density

Dynamic Binding Capacity Measurement.

The results of IgG dynamic binding capacity measurements for the SP-functionalized fiber media of example 12-6 are provided in Table 8 below. 1.0 g of the media was packed into an 11 mm internal diameter Vantage column and compressed to a bed depth of 2.9 cm (2.75 mL column volume, 0.36 g/mL fiber packing density). The dynamic binding capacity measurements were conducted over a range of linear velocities from 60 cm/hr to 1200 cm/hr. These velocities correspond to residence times of 9 seconds to 180 seconds. The fiber media of example 12-6 demonstrates IgG dynamic binding capacities in the range of 30-40 mg/mL.

TABLE 8

IgG DBC values for the SP-tentacle functionalized Allasso winged fiber cation-exchange media at 1, 5, 10, and 50% breakthrough at varying linear velocities (RT = residence time). Challenge: 2.0 g/L polyclonal human IgG (SeraCare Life Sciences, Milford, MA) in 50 mM acetate, pH 5.

| Example 12-6 | DBC (mg/mL) | | | | | | |
|---|---|---|---|---|---|---|---|
| % Breakthrough | 60 cm/hr (RT 174 sec) | 200 cm/hr (RT 52 sec) | 200 cm/hr (RT 52 sec) | 200 cm/hr (RT 52 sec) | 400 cm/hr (RT 26 sec) | 800 cm/hr (RT 13 sec) | 1200 cm/hr (RT 9 sec) |
| 1 | 36 | 31 | 32 | 31 | 29 | 27 | 25 |
| 5 | 38 | 32 | 33 | 33 | 30 | 28 | 26 |
| 10 | 38 | 33 | 33 | 33 | 31 | 28 | 27 |
| 50 | 44 | 39 | 39 | 39 | 36 | 34 | 32 |

Example 13

Graft Polymerization of Un-Modified Nylon Fibers.

Into 6×200 mL bottles were added glycidyl methacrylate (GMA), water, nylon fibers (Allasso Industries) and 1 M $HNO_3$ solution (in the amounts described in the table below). A 0.4 M solution of ammonium cerium(IV) nitrate (CAN) in 1 M $HNO_3$ were added to each bottle. The reaction bottles were capped and the mixtures were heated to 35° C. for 18 hours.

After cooling to room temperature, the fiber solids from each bottle were washed with a solution of 0.2 M ascorbic acid in 0.5 M sulfuric acid (3×50 mL), DI water (3×50 mL), 1 M sodium hydroxide solution (3×50 mL), DI water (3×50 mL) and acetone (1×50 mL). The material was placed in an oven to dry at 40° C. for 12 hrs.

Obtained samples of a white fibrous solid (see Table 9 for recovery and weight add-on data).

TABLE 9

Cerium redox graft polymerization compositions and recovery data.

| Reaction # | Allasso fiber (g) | GMA monomer, g (mmol) | CAN (mM) | $HNO_3$ (mM) | water (mL) | Product wt, g (% add-on)[1] |
|---|---|---|---|---|---|---|
| Example 13-1 | 1.5 g | 0.53 g (4 mmol) | 5 mmol | 150 mmol | 62.8 mL | 1.62 g (+8%) |
| Example 13-2 | 1.5 g | 1.07 g (8 mmol) | 3 mmol | 75 mmol | 68.9 mL | 2.13 g (+42%) |
| Example 13-3 | 1.5 g | 0.53 g (4 mmol) | 1 mmol | 30 mmol | 72.6 mL | 1.62 g (+8%) |
| Example 13-4 | 1.5 g | 0.11 g (1 mmol) | 3 mmol | 75 mmol | 68.9 mL | 1.62 g (+8%) |
| Example 13-5 | 1.5 g | 0.53 g (4 mmol) | 5 mmol | 50 mmol | 70.3 mL | 1.35 g (na, spill) |
| Example 13-6 | 1.5 g | 1.07 g (8 mmol) | 3 mmol | 25 mmol | 72.7 mL | 2.01 g (+34%) |

[1]Calculated based on ⅓ isolated fraction

Diethylamine-Functionalization of Epoxy-Functionalized Fibers.

Into 6×250 mL bottles were added portions of the damp GMA-functionalized fibers from the example above, and a solution of 25 wt % diethylamine (aq.) (in the amounts described in the table below). The mixtures were agitated at room temperature for 3 hours.

The fiber solids were subsequently washed with DI water (3×50 mL) and ethanol (1×50 mL). The material was placed in an oven to dry at 40° C. for 12 hrs.

Obtained samples of a white fibrous solid (see Table 10 for recovery and weight add-on data).

TABLE 10

Compositions for the modification of epoxy-functionalized fibers with diethylamine and recovery data.

| Reaction # | damp GMA-fiber (g) | 25% Et$_2$N, aq. (mL) | Product wt, g (% add-on)[1] |
|---|---|---|---|
| Example 13-1B | 3.24 | 100 mL | 1.08 g (+8%) |
| Example 13-2B | 4.88 | 100 mL | 1.32 g (+32%) |
| Example 13-3B | 1.93 | 100 mL | 1.08 g (+8%) |
| Example 13-4B | 3.00 | 100 mL | 1.00 g (+0%) |
| Example 13-5B | 3.51 | 100 mL | 1.22 g (+22%) |
| Example 13-6B | 4.34 | 100 mL | 1.34 g (+34%) |

[1]Calculated based on 2/3 fraction of initial 1.5 g fiber charge.

Static Binding Capacity Measurement.

The results of static binding capacity measurements for BSA are provided in Table 11 below. Depending on the GMA-tentacle grafting density, the diethylamine-functionalized tentacle fiber media can demonstrate BSA static binding capacities over a wide range of values. In this series, we found the Example 13-2B and Example 13-3B compositions gave BSA SBC values comparable to bead-based anion-exchange media employed in commercial biomolecule chromatography applications.

TABLE 11

Static binding capacity measurement. Challenge: 2 g/L bovine serum albumin (BSA) in 25 mM tris buffer (pH 8).

| Sample | Amt (g) | BSA Bound (mg) | SBC (mg/g) | SBC (mg/mL)[1] |
|---|---|---|---|---|
| Example 13-1B | 0.099 | 2.76 | 28 | 9 |
| Example 13-2B | 0.096 | 14.60 | 152 | 50 |
| Example 13-3B | 0.102 | 18.80 | 184 | 60 |
| Example 13-4B | 0.109 | 1.41 | 13 | 4 |
| Example 13-5B | 0.102 | 4.26 | 42 | 14 |
| Example 13-6B | 0.112 | 6.36 | 57 | 19 |
| Allasso 3 kg lot | 0.086 | 0.21 | 2 | 1 |

[1]Based on a 0.33 g/mL fiber packing density

Dynamic Binding Capacity Measurement.

The results of BSA dynamic binding capacity measurements for the diethylamine-functionalized fiber media of Example 13-3B are provided in Table 12 below. 0.5 g of the media was packed into an 11 mm internal diameter Vantage column and compressed to a bed depth of 1.5 cm (1.42 mL column volume, 0.35 g/mL fiber packing density). The dynamic binding capacity measurement was conducted at a linear velocity of 200 cm/hr. This velocity corresponds to a residence time of 27 seconds. The fiber media of Example 13-3B demonstrates, a BSA dynamic binding capacity of 30 mg/mL at 10% breakthrough.

TABLE 12

BSA DBC values for the diethylamine-tentacle functionalized Allasso winged fiber anion-exchange media at 1, 5, 10, and 50% breakthrough at 200 cm/hr (RT = residence time). Challenge: 2 g/L bovine serum albumin (BSA) in 25 mM Tris buffer (pH 8).

| Example 13-3B % Breakthrough | DBC (mg/mL) 200 cm/hr (RT 27 sec) |
|---|---|
| 1 | 25 |
| 5 | 29 |
| 10 | 31 |
| 50 | 39 |

Example 14

Graft Polymerization of Un-Modified Nylon Fibers.

Into a 500 mL bottle were added glycidyl methacrylate (GMA, 1.70 g, 12 mmol), and water (232.8 mL). 5 g of Allasso nylon fibers were added to the solution. 1 M HNO$_3$ solution (7.22 mL, 7.2 mmol) were added to the reaction mixture, followed by addition of a 0.4 M solution of ammonium cerium(IV) nitrate in 1 M HNO$_3$ (0.602 mL, 0.240 mmol)

The reaction mixture was heated to 35° C. for 1 hour.

After cooling to room temperature, the solids were washed with DI water (3×100 mL) and the damp material (12.21 g) was used immediately in the following step.

Q-Functionalization of Epoxy-Functionalized Fibers.

Into 4×250 mL bottles were added portions of the damp GMA-functionalized fibers from the example above, and a solution of 50 wt % trimethylamine (aq.) in methanol (in the amounts described in Table 13 below). The mixtures were agitated at room temperature for 18 hours.

The fiber solids were subsequently washed with a solution of 0.2 M ascorbic acid in 0.5 M sulfuric acid (3×50 mL), DI water (3×50 mL), 1 M sodium hydroxide solution (3×50 mL), DI water (3×50 mL) and ethanol (1×50 mL). The material was placed in an oven to dry at 40° C. for 12 hrs.

Obtained samples of a white fibrous solid (see Table 13 for recovery and weight add-on data).

TABLE 13

Compositions for the modification of epoxy-functionalized fibers with trimethylamine and recovery data.

| Reaction # | damp GMA-fiber(g) | 50% Me$_3$N, aq. (mL) | Methanol (mL) | Product wt, g (% add-on) |
|---|---|---|---|---|
| Example 14B | 2.44 g | 100 mL | 0 mL | 1.09 g (+9%) |
| Example 14C | 2.44 g | 80 mL | 20 mL | 1.02 g (+2%) |
| Example 14D | 2.44 g | 50 mL | 50 mL | 1.04 g (+4%) |
| Example 14E | 2.44 g | 20 mL | 80 mL | 0.97 g (−3%) |
| Example 14 | 2.44 g | — | — | 1.09 g (+9%) |

Static Binding Capacity Measurement.

The results of static binding capacity measurements for BSA are provided in Table below. The Q-functionalized tentacle fiber media afforded BSA static, binding capacities in the range of 30 mg/mL. In this series, we found the Example 14C and Example 14D compositions gave the highest BSA SBC values, comparable to bead-based anion-exchange media employed in commercial biomolecule chromatography applications.

TABLE 14

Static binding capacity measurement. Challenge: 2 g/L bovine serum albumin (BSA) in 25 mM tris buffer (pH 8).

| Sample | Amt (g) | BSA Bound (mg) | SBC (mg/g) | SBC (mg/mL)[1] |
|---|---|---|---|---|
| Example 14 (unmodified GMA-grafted fiber) | 0.097 | −0.09 | −1 | 0 |
| Example 14B | 0.100 | 8.76 | 88 | 29 |
| Example 14C | 0.097 | 10.10 | 104 | 34 |
| Example 14D | 0.099 | 10.40 | 105 | 34 |
| Example 14E | 0.104 | 9.66 | 93 | 30 |

[1]Based on a 0.33 g/mL fiber packing density

Dynamic Binding Capacity Measurement.

The results of BSA dynamic binding capacity measurements for a Q-functionalized fiber media prepared according to Example 14C are provided in Table 15 below. 1.0 g of the media was packed into an 11 mm internal diameter Vantage column and compressed to a bed depth of 3.0 cm (2.85 mL column volume, 0.35 g/mL fiber packing density). The dynamic binding capacity measurements were conducted over a range of linear velocities from 60 cm/hr to 1200 cm/hr. These velocities correspond to residence times of 9 seconds to 180 seconds. The fiber media of Example 14C demonstrates BSA dynamic binding capacities in the range of 30-40 mg/mL.

TABLE 15

BSA DBC values for the Q-tentacle functionalized Allasso winged fiber anion-exchange media at 1, 5, 10, and 50% breakthrough at varying linear velocities (RT = residence time). Challenge: 2 g/L bovine serum albumin (BSA) in 25 mM Tris buffer (pH 8).

| Example 14C | DBC (mg/mL) | | | | | | |
|---|---|---|---|---|---|---|---|
| % Breakthrough | 60 cm/hr (RT 180 sec) | 200 cm/hr (RT 54 sec) | 200 cm/hr (RT 54 sec) | 200 cm/hr (RT 54 sec) | 1200 cm/hr (RT 9 sec) | 800 cm/hr (RT 14 sec) | 1200 cm/hr (RT 9 sec) |
| 1 | 34 | 29 | 25 | 30 | 29 | 26 | 25 |
| 5 | 36 | 35 | 36 | 32 | 30 | 28 | 27 |
| 10 | 37 | 36 | 37 | 33 | 31 | 29 | 28 |
| 50 | 43 | 43 | 44 | 39 | 38 | 36 | 35 |

Example 15

Graft Polymerization of Un-Modified Nylon Fibers.

Into a 500 mL bottle were added hydroxyethylmethacrylate (HEMA, 1.69 g, 13 mmol), and water (232.5 mL). 5.00 g of Allasso nylon fibers were added to the solution. 1 M HNO$_3$ solution (7.21 mL, 7.2 mmol) were added to the reaction mixture, followed by addition of a 0.4 M solution of ammonium cerium(IV) nitrate in 1 M HNO$_3$ (0.601 mL, 0.240 mmol).

The reaction mixture was heated to 35° C. for 1 hour.

After cooling to room temperature, the solids were washed with a solution of 0.2 M ascorbic acid in 0.5 M sulfuric acid (3×100 mL), DI water (3×100 mL), 1 M sodium hydroxide solution (3×100 mL), DI water (3×100 mL) and ethanol (1×100 mL). The material was placed in an oven to dry at 40° C. for 12 hrs.

Obtained 5.58 g as a white fibrous solid.

Example 16

Sulfation of Poly(HEMA)-Functionalized Fibers.

Into a 500 mL 3 necked flask under argon with a magnetic stirbar and 3 N NaOH sodium hydroxide bubbler were added acetic acid and cooled to 0° C. Chlorosulfonic acid (5.0 g, 43 mmol) was added. 2.5 g of the poly(HEMA)-functionalized fibers from the above example were added to the reaction mixture. The reaction was allowed to warm to room temperature and stirred for 1 hour.

The fiber solids were subsequently neutralized by addition of 5 mL water and 300 mL 1 M sodium carbonate solution. Solid sodium carbonate was added to the reaction mixture in portions until the pH>7. The fiber solids were subsequently washed with a solution of 1 M sodium carbonate (3×100 mL), DI water (3×100 mL) and ethanol (1×100 mL). The material was placed in an oven to dry at 40° C. for 12 hrs.

Obtained 3.64 g of a white gummy solid.

Comparative Example 1

Graft Polymerization of Un-Modified EVOH Fibers.

Into 4×30 mL bottles were added 2-acrylamido-2-methyl-1-propanesulfonic acid sodium salt solution (AmPS-Na, 50% aq.), water, and EVOH fibers (Engineered Fiber Technologies, S030-0.5 d×5 mm). The reaction mixture was purged under vacuum and backfilled with nitrogen three times. 1 M HNO$_3$ solution and a 0.4 M solution of ammonium cerium (IV) nitrate (CAN) in 1 M HNO$_3$ were added to each bottle (in the amounts described in Table 16 below). The reaction bottles were capped and the mixtures were heated to 40° C. for 12 hours.

After cooling to room temperature, the fiber solids from each bottle were washed with DI water (3×30 mL), a solution of 0.2 M ascorbic acid in 0.5 M sulfuric acid (3×30 mL), DI water (3×30 mL), 1 M sodium hydroxide solution (2×30 mL), DI water (3×30 mL) and methanol (2×30 mL). The material was placed in an oven to dry at 40° C. for 8 hrs.

Obtained samples of a white fibrous solid (see Table 16 for recovery and % yield data).

TABLE 16

Cerium redox graft polymerization compositions and recovery data.

| Reaction # | EVOH fiber (g) | AmPS-Na monomer, g (mmol) | CAN (mM) | HNO$_3$ (mM) | water (mL) | Product wt, g (% yield) |
|---|---|---|---|---|---|---|
| Comparative Example 1-1 | 0.5 g | 4.58 g (20 mmol) | 2.5 mmol | 25 mmol | 10.2 mL | 0.42 g (84%) |
| Comparative Example 1-2 | 0.5 g | 2.29 g (10 mmol) | 5.0 mmol | 25 mmol | 14.7 mL | 0.45 g (90%) |
| Comparative Example 1-3 | 0.5 g | 1.15 g (5 mmol) | 1.0 mmol | 25 mmol | 17.2 mL | 0.45 g (90%) |
| Comparative Example 1-4 | 0.5 g | 0.46 g (2 mmol) | 2.5 mmol | 25 mmol | 18.5 mL | 0.43 g (86%) |

Comparative Example 2

Graft Polymerization of Un-Modified PVA Fibers.

Into 4×30 mL bottles were added 2-acrylamido-2-methyl-1-propanesulfonic acid sodium salt solution (AmPS-Na, 50% aq.), water, and PVA fibers (Engineered Fiber Technologies, VPB 052×3 mm). The reaction mixture was purged under vacuum and backfilled with nitrogen three times. 1 M HNO$_3$ solution and a 0.4 M solution of ammonium cerium(IV) nitrate (CAN) in 1 M HNO$_3$ were added to each bottle (in the amounts described in Table 17 below). The reaction bottles were capped and the mixtures were heated to 40° C. for 12 hours.

After cooling to room temperature, the fiber solids from each bottle were washed with DI water (3×30 mL), a solution of 0.2 M ascorbic acid in 0.5 M sulfuric acid (3×30 mL), DI water (3×30 mL), 1 M sodium hydroxide solution (2×30 mL), DI water (3×30 mL) and methanol (2×30 mL). The material was placed in an oven to dry at 40° C. for 8 hrs.

Obtained samples of a white fibrous solid (see Table 17 for recovery and % yield data).

TABLE 17

Cerium redox graft polymerization compositions and recovery data.

| Reaction # | PVA fiber (g) | AmPS-Na monomer, g (mmol) | CAN (mM) | HNO$_3$ (mM) | water (mL) | Product wt, g (% yield) |
|---|---|---|---|---|---|---|
| Comparative Example 2-1 | 0.5 g | 4.58 g (20 mmol) | 2.5 mmol | 25 mmol | 10.2 mL | 0.45 g (90%) |
| Comparative Example 2-2 | 0.5 g | 2.29 g (10 mmol) | 5.0 mmol | 25 mmol | 14.7 mL | 0.53 g (106%) |
| Comparative Example 2-3 | 0.5 g | 1.15 g (5 mmol) | 1.0 mmol | 25 mmol | 17.2 mL | 0.44 g (88%) |
| Comparative Example 2-4 | 0.5 g | 0.46 g (2 mmol) | 2.5 mmol | 25 mmol | 18.5 mL | 0.42 g (84%) |

Static Binding Capacity Measurement.

The results of static binding capacity measurements for IgG are provided in Table 18 below. The SP-functionalized tentacle media based on an EVOH fiber base matrix (Comparative Example 1) demonstrates only a low IgG static binding capacity. The SP-functionalized tentacle media based on a PVA fiber base matrix (Comparative Example 2) demonstrates only a slightly higher IgG static binding capacity for certain compositions (Comparative Example 2-1). In all cases, the IgG SBC values are much lower than bead-based cation-exchange media employed in commercial biomolecule chromatography applications. These examples serve to illustrate the benefit of surface area enhancement demonstrated by the winged fiber media from Allasso Industries. If similar surface area enhancement is practiced on a PVA or EVOH type base matrix, high IgG binding capacities may be obtained after direct surface functionalization using the ceric ion redox grafting procedure described herein.

TABLE 18

Static binding capacity measurement. Challenge: 2 g/L polyclonal human IgG (SeraCare Life Sciences, Milford, MA) in 50 mM Sodium Acetate (pH 5).

| Sample | Amt (g) | IgG Bound (mg) | SBC (mg/g) | SBC (mg/mL)[1] |
|---|---|---|---|---|
| Comparative Example 1-1 | 0.111 | −0.01 | 0 | 0 |
| Comparative Example 1-2 | 0.098 | 0.35 | 4 | 1 |
| Comparative Example 1-3 | 0.101 | 0.06 | 1 | 0 |
| Comparative Example 1-4 | 0.104 | −0.01 | 0 | 0 |
| Comparative Example 2-1 | 0.114 | 1.83 | 16 | 5 |
| Comparative Example 2-2 | 0.099 | −0.34 | −3 | −1 |
| Comparative Example 2-3 | 0.107 | −0.12 | −1 | 0 |
| Comparative Example 2-4 | 0.108 | −0.34 | −3 | −1 |
| EVOH S030-0.5d 1 | 0.099 | −0.34 | −3 | −1 |
| PVA VPB052x3 mm 1 | 0.118 | 0.38 | 3 | 1 |

[1]Based on a 0.33 g/mL fiber packing density

Example 16

Nylon Fiber Surface Modification with HPA/MBAm 95/5.

Into a 2000 mL 3-necked roundbottom flask with mechanical stirrer, reflux condenser, and temperature controller were added hydroxypropylacrylate (HPA, 13.7 g, 95 mmol), N,N'-methylenebis(acrylamide) (MBAm, 0.77 g, 5 mmol) and water (710 mL). 16.8 g of loose nylon fibers (Allasso Industries, #090602PA6C) were added to the mixture. Ammonium persulfate (1.60 g, 7 mmol) was added. The wet solids were heated to 80° C. for 4 hours.

After cooling to room temperature, the solids were transferred to a Buchner funnel and washed with hot water (3×500 mL) and methanol (1×500 mL). The material was allowed to dry under vacuum for 20 minutes. The material was transferred to an oven and dried at 40° C. for 18 hours.

Obtained 17.6 g as white fibers.

Example 17

Graft Polymerization of HPA/MBAm Modified Nylon Fibers.

Into 4×200 mL bottles were added glycidyl methacrylate (GMA), water, HPA/MBAm modified nylon fibers (Example 16) and 1 M HNO$_3$ solution (in the amounts described in Table 19 below). A 0.4 M solution of ammonium cerium(IV) nitrate (CAN) in 1 M HNO$_3$ were added to each bottle. The reaction bottles were capped and the mixtures were heated to 35° C. for 12 hours.

After cooling to room temperature, the fiber solids from each bottle were washed with DI water (3×150 mL) and methanol (1×150 mL). The material was placed in an oven to dry at 40° C. for 12 hrs.

Obtained samples of a white fibrous solid (see Table 19 for recovery and weight add-on data).

TABLE 19

Cerium redox graft polymerization compositions and recovery data.

| Reaction # | HPA/MBAm fiber (g) | GMA monomer, g (mmol) | CAN (mM) | HNO$_3$ (mM) | water (mL) | Product wt, g (% add-on) |
|---|---|---|---|---|---|---|
| Example 17-1 | 1.5 g | 5.69 g (40 mmol) | 5 mM | 50 mM | 150 mL | 3.87 g, (+158) |
| Example 17-2 | 1.5 g | 3.41 g (24 mmol) | 5 mM | 50 mM | 150 mL | 2.90 g (+93%) |
| Example 17-3 | 1.5 g | 1.14 g (8 mmol) | 5 mM | 50 mM | 150 mL | 2.21 g (+47%) |
| Example 17-4 | 1.5 g | 0.57 g (4 mmol) | 5 mM | 50 mM | 150 mL | 1.82 g (+21%) |

Example 18

Nylon Fiber Surface Modification with Recombinant Protein a Affinity Ligand, rSPA.

Into a 250 mL bottle were added 1 M sodium bicarbonate (100 mL), recombinant protein A (rSPA #RN091139, 150 mg, as a 47.5 mg/mL solution in water) and water (90 mL). GMA-grafted fibers (350 mg) from the example 17-4 above were added to the reaction mixture. The mixture was heated at 37° C. for 2.5 hours.

After cooling to room temperature, the solids were transferred to a Buchner funnel and washed with 0.1 M sodium bicarbonate (3×100 mL). The wet fiber solids were suspended in 100 mL of a 10 wt % thioglycerol solution in 0.2 M sodium bicarbonate/0.5 M sodium chloride solution. The mixture was stirred at room temperature overnight.

The solids were transferred to a Buchner funnel and washed with a solution of 0.1 M TRIZMA base with 0.15 M sodium chloride (1×75 mL), 0.05 M acetic acid solution (1×75 mL). The TRIZMA base and acetic acid washing cycles were repeated two additional times. The fiber solids were finally washed with DI water (1×75 mL) and 20 wt % ethanol (1×75 mL). The fiber solids were stored in 20 wt % ethanol solution.

Static Binding Capacity Measurement.

The results of IgG static binding capacity measurements for a protein A-functionalized fiber media prepared according to example 18 are provided in Table 20 below. The protein A-functionalized tentacle fiber media afforded IgG static binding capacities in the range of 4 mg/mL. Further optimization of the protein A ligand coupling procedure will provide increased IgG static binding capacities for low-cost biomolecule affinity chromatography applications.

TABLE 20

Static binding capacity measurement. Challenge: 2 g/L polyclonal human IgG (SeraCare Life Sciences, Milford, MA) in phosphate buffered saline (pH 7.4).

| Sample | Amt (g) | IgG Bound (mg) | SBC (mg/g) | SBC (mg/mL)[1] |
|---|---|---|---|---|
| Example 18A | 0.500 | 4.22 | 8 | 3 |
| Example 18B | 0.500 | 5.67 | 11 | 4 |

[1]Based on a 0.33 g/mL fiber packing density

Dynamic Binding Capacity Measurement.

The results of IgG dynamic binding capacity measurements for the protein A-functionalized fiber media of example 18 are provided in Table 21 below. 0.35 g of the media was packed into an 11 mm internal diameter Vantage column and compressed to a bed depth of 1.1 cm (1.04 mL column volume, 0.34 g/mL fiber packing density). The dynamic binding capacity measurements were conducted over a range of linear velocities from 60 cm/hr to 800 cm/hr. These velocities correspond to residence times of 5 seconds to 60 seconds. The fiber media of example 18 demonstrates IgG dynamic binding capacities in the range of 5 mg/mL. Further optimization of the protein A ligand coupling procedure will provide increased IgG dynamic binding capacities for low-cost biomolecule affinity chromatography applications.

TABLE 21

IgG DBC values for the protein A-functionalized Allasso winged fiber affinity
chromatography media at 1, 5, 10, and 50% breakthrough at varying linear velocities (RT =
residence time). Challenge: 2 g/L polyclonal human IgG (SeraCare Life Sciences, Milford, MA)
in phosphate buffered saline (pH 7.4).

| Example 18 | DBC (mg/mL) | | | | | |
|---|---|---|---|---|---|---|
| % Breakthrough | 60 cm/hr (RT 60 sec) | 60 cm/hr (RT 60 sec) | 60 cm/hr (RT 60 sec) | 200 cm/hr (RT 18 sec) | 400 cm/hr (RT 9 sec) | 800 cm/hr (RT 5 sec) |
| 1 | 5 | 4 | 4 | 4 | 5 | 4 |
| 5 | 5 | 5 | 5 | 5 | 5 | 5 |
| 10 | 6 | 5 | 5 | 5 | 5 | 5 |
| 50 | 7 | 7 | 7 | 7 | 7 | 7 |

Example 19

Flow-Through Graft Polymerization of HPA/MBAm Modified Nylon Fibers.

Into a 22 mm internal diameter Vantage chromatography column was added a slurry of HPA/MBAm modified nylon fibers from example 16 above (1.52 g fibers in 100 mL DI water). A vacuum was used to draw excess liquid through the column and to facilitate the compression of the staple fibers. After the slurry was transferred to the column, the top header of the column was installed, and the header compressed to give a final column volume of 4.54 mL (1.2 cm bed depth). Into a 250 mL 3-necked flask with magnetic stirbar, reflux condenser, temperature controller, and heating mantle were added 2-acrylamido-2-methyl-1-propanesulfonic acid sodium salt solution (AmPS-Na, 50% aq., 23.0 g, 100 mmol) and water (53.5 mL). The monomer solution was sparged with argon gas for 10 minutes. A 0.4 M solution of ammonium cerium(IV) nitrate (CAN) in 1 M $HNO_3$ (0.62 mL, 0.250 mmol) and 1 M $HNO_3$ solution (2.5 mL, 2.5 mmol) was added to the reaction mixture and the reaction mixture was heated to 35° C. This monomer solution was pumped through the Vantage column at a rate of 3.5 mL/min for 12 hours. The viscosity of the monomer solution was found to increase during the course of the reaction; this resulted in a substantial decrease in the flow rate of the monomer solution through the column sometime after three hours.

After cooling to room temperature, the fiber solids from the vantage column were removed and washed with a solution of 0.2 M ascorbic acid in 0.5 M sulfuric acid (3×150 mL), DI water (3×150 mL), 1 M sodium hydroxide solution (3×150 mL), DI water (3×150 mL) and methanol (1×150 mL). The material was placed in an oven to dry at 40° C. for 12 hrs.

Obtained 1.52 g as a white fibrous solid.

Static Binding Capacity Measurement.

The results of static binding capacity measurements for IgG are provided in Table below. The SP-functionalized tentacle fiber media prepared through a flow-through graft polymerization process demonstrates IgG static binding capacities comparable to bead-based cation-exchange media employed in commercial biomolecule chromatography applications. The HPA/MBAm modified fiber precursor (Example 16) displays only minimal IgG SBC.

TABLE 22

Static binding capacity measurement. Challenge: 2 g/L polyclonal
human IgG (SeraCare Life Sciences, Milford, MA) in 50 mM acetate
(pH 5).

| Sample | Amt (g) | IgG Bound (mg) | SBC (mg/g) | SBC (mg/mL)[1] |
|---|---|---|---|---|
| Example 19 | 0.094 | 16.41 | 175 | 57 |
| Example 16 (HPA/MBAm modified fibers) | 0.100 | 0.54 | 5 | 2 |

[1]Based on a 0.33 g/mL fiber packing density

Dynamic Binding Capacity Measurement.

The results of IgG dynamic binding capacity measurements for the SP-functionalized fiber media of example 19 are provided in Table 23 below. 0.64 g of the media was packed into an 11 mm internal diameter Vantage column and compressed to a bed depth of 2.0 cm (1.90 mL column volume, 0.32 g/mL fiber packing density). The dynamic binding capacity measurements were conducted at a linear velocity of 200 cm/hr. This velocity corresponds to a residence time of 36 seconds. The fiber media of example 19 demonstrates an IgG dynamic binding capacity of 40 mg/mL.

TABLE 23

IgG DBC values for the SP-tentacle functionalized Allasso winged fiber
cation-exchange media at 1, 5, 10, and 50% breakthrough at varying
linear velocities (RT = residence time, nd = no data). Challenge:
2.0 g/L polyclonal human IgG (SeraCare Life Sciences, Milford, MA) in
50 mM acetate, pH 5.

| | DBC (mg/mL) | | |
|---|---|---|---|
| % Breakthrough | 200 cm/hr (RT 36 sec) | 200 cm/hr (RT 36 sec) | 200 cm/hr (RT 36 sec) |
| 1 | 35 | 34 | 35 |
| 5 | 38 | 37 | 37 |
| 10 | 41 | 40 | 40 |
| 50 | nd | nd | 59 |

Example 20

Graft Co-Polymerization of Un-Modified Nylon Fibers.

Into 4×250 mL bottles were added glycidyl methacrylate (GMA), (3-acrylamidopropyl)trimethylammonium chloride solution (APTAC, 75 wt % solution in water), water, winged nylon fibers (Allasso Industries) and 1 M $HNO_3$ solution (in the amounts described in the table below). A 0.4 M solution of ammonium cerium(IV) nitrate (CAN) in 1 M $HNO_3$ were added to each bottle. The reaction bottles were capped and the mixtures were heated to 35° C. for 3 hours.

After cooling to room temperature, the fiber solids from each bottle were washed with acetone (3×100 mL). The damp material was placed in an oven to dry at 40° C. for 12 hrs.

Obtained samples of a white fibrous solid (see Table 24 for recovery and weight add-on data).

TABLE 24

Cerium redox graft polymerization compositions and recovery data.

| Reaction # | Allasso fiber (g) | GMA monomer, g (mmol) | APTAC monomer g (mmol) | CAN (mM) | HNO$_3$ (mM) | water (mL) | Product wt, g (% add-on) |
|---|---|---|---|---|---|---|---|
| Example 20-1 | 1.5 g | 3.84 g (27 mmol) | 0.62 g (3 mmol) | 10 mM | 300 mM | 50.6 mL | 3.13 g, (+108%) |
| Example 20-2 | 1.5 g | 2.88 g (20 mmol) | 0.47 g (3 mmol) | 10 mM | 300 mM | 50.6 mL | 2.88 g (+92%) |
| Example 20-3 | 1.5 g | 1.92 g (14 mmol) | 0.31 g (2 mmol) | 10 mM | 300 mM | 50.6 mL | 2.23 g (+49%) |
| Example 20-4 | 1.5 g | 0.96 g (7 mmol) | 0.16 g (1 mmol) | 10 mM | 300 mM | 50.6 mL | 1.75 g (+16%) |

Example 21

Poly(Allylamine) Modification of Epoxy-Functionalized Fibers.

Into a 30 mL bottle were added GMA/APTAC grafted fibers from Example 20-2 above (0.5 g), water (10 mL). 40 wt % poly(allylamine) hydrochloride solution (1.25 g of 40 wt % solution) and 1.0 M sodium hydroxide (10 mL). The reaction mixture was heated to 35° C. for 18 hours.

After cooling to room temperature, the solids were washed with DI water (3×50 mL) and acetone (1×50 mL).

The damp material was placed in an oven to dry at 40° C. for 12 hrs.

Obtained 0.48 g as a light yellow fibrous solid.

Example 22

Poly(Allylamine) Modification of Sulfopropyl-Functionalized Fibers.

In a 500 mL beaker equipped with a magnetic stir bar were added 1.0 g of the sulfopropyl-functionalized fibers of Example 2 and a solution of polyallylamine in water (PAA MW=15 kDa, 20% (w/w), 75 mL). Poly(ethyleneglycol)diglycidyl ether (750 µL, Aldrich #475696) was added and the mixture was stirred rapidly for 5 minutes at room temperature and then quenched with 250 mL water. The mixture was filtered through a medium glass frit filter and washed with water (3×250 mL). The fibers were dried at 40° C. overnight. (Example 22)

Example 23

Poly(Allylamine) Modification of Sulfopropyl-Functionalized Fibers.

In a 500 mL beaker equipped with a magnetic stir bar were added 1.0 g of the sulfopropyl-functionalized fibers of Example 2 and a solution, of polyallylamine in water (PAA MW=15 kDa, 20% (w/w), 75 mL). Poly(ethyleneglycol)diglycidyl ether (750 µL, Aldrich #475696) was added and the mixture was stirred rapidly for 10 minutes at room temperature and then quenched with 250 mL water. The mixture was filtered through a medium glass frit filter and washed with water (3×250 mL). The fibers were dried at 40° C. overnight. (Example 23)

Example 24

Poly(Allylamine) Modification of Sulfopropyl-Functionalized Fibers.

In a 500 mL beaker equipped with a magnetic stir bar were added 1.0 g of the poly(allylamine)-functionalized fibers of example 23 and a solution of polyallylamine in water (PAA MW=15 kDa, 20% (w/w), 75 mL). Poly(ethyleneglycol)diglycidyl ether (750 µL, Aldrich #475696) was added and the mixture was stirred rapidly for 10 minutes at room temperature and then quenched with 250 mL water. The mixture was filtered through a medium glass frit filter and washed with water (3×250 mL). The fibers were dried at 40° C. overnight. (Example 24)

Static Binding Capacity Measurement.

The results of static binding capacity measurements for BSA are provided in Table 25 below. The poly(allylamine)-functionalized fiber media afforded BSA static binding capacities in the range of 20-60 mg/mL. In this series, we found that the composition from Example 24 gave the highest BSA SBC values, comparable to bead-based anion-exchange media employed in commercial biomolecule chromatography applications.

TABLE 25

Static binding capacity measurement. Challenge: 2 g/L bovine serum albumin (BSA) in 50 mM tris buffer (pH 8).

| Sample | Amt (g) | BSA Bound (mg) | SBC (mg/g) | SBC (mg/mL)[1] |
|---|---|---|---|---|
| Example 22 | 0.01 | 0.60 | 60 | 20 |
| Example 23 | 0.01 | 0.89 | 89 | 29 |
| Example 24 | 0.01 | 1.72 | 172 | 57 |
| Example 2 | 0.01 | −0.03 | −3 | −1 |

[1]Based on a 0.33 g/mL fiber packing density

Dynamic Binding Capacity Measurement.

The results of BSA dynamic binding capacity measurements for the poly(allylamine)-functionalized fiber media of Example 24 are provided in Table 26 below. 1.0 g of the media was packed into an 11 mm internal diameter Vantage column and compressed to a bed depth of 3.0 cm (2.85 mL column volume, 0.35 g/mL fiber packing density). The dynamic binding capacity measurement was conducted at a linear velocity of 200 cm/hr. This velocity corresponds to a residence time of 54 seconds. The fiber media of Example 24 demonstrates a BSA dynamic binding capacity of 50 mg/mL at 10% breakthrough.

TABLE 26

BSA DBC values for the poly(allylamine)-functionalized Allasso winged fiber anion-exchange media at 1, 5, 10, and 50% breakthrough at 200 cm/hr (RT = residence time). Challenge: 0.5 g/L BSA in 25 mM Tris, pH 8.

| Example 24 % Breakthrough | DBC (mg/mL) 200 cm/hr (RT 54 sec) |
|---|---|
| 1 | 44 |
| 5 | 47 |
| 10 | 49 |
| 50 | 62 |

Example 25

Nylon Fiber Surface Modification with HPA/MBAm 95/5.

Into a 1000 mL 3-necked roundbottom flask with mechanical stirrer, reflux condenser, and temperature controller were added hydroxypropylacrylate (HPA, 13.7 g, 95 mmol), N,N'-methylenebis(acrylamide) (MBAm, 0.77 g, 5 mmol) and water (710 mL). 16.8 g of loose nylon fibers (Allaso Industries, #090602PA6C) were added to the mixture. Ammonium persulfate (1.60 g, 7 mmol) was added. The wet solids were heated to 80° C. for 4 hours.

After cooling to room temperature, the solids were transferred to a Buchner funnel and washed with hot water (3×500 mL) and methanol (1×500 mL). The material was allowed to dry under vacuum for 30 minutes. The material was transferred to an oven and dried at 40° C. for 12 hours.

Obtained 17.3 g as white fibers.

Example 26

Ceric Ion Redox Graft Polymerization of HPA/MBAm Modified, High Surface Area Fibers With Pendant Sulfopropyl Cation-Exchange Functionality Graft Polymerization of HPA/MBAm Modified Nylon Fibers.

Into a 200 mL 3-necked roundbottom flask with mechanical stirrer, reflux condenser, and temperature controller were added 2-Acrylamido-2-methyl-1-propanesulfonic acid sodium salt (AMPS-Na, 23.1 g, 100 mmol), and water (76.3 mL). 2.50 g of HPA/MBAm modified nylon fibers (Example 25) were added to the solution. The reaction mixture was purged under vacuum and backfilled with nitrogen gas for 3 cycles.

A 0.4 M solution of ammonium cerium(IV) nitrate in 1 M $HNO_3$ (0.620 mL, 0.250 mmol) and 1 M $HNO_3$ solution (2.46 mL, 2.46 mmol) were added to the reaction mixture.

The reaction mixture was heated to 35° C. for 18 hours.

After cooling to room temperature, the solids were washed with a solution of 0.2 M ascorbic acid in 0.5 M sulfuric acid (3×150 mL), DI water (3×150 mL), 1 M sodium hydroxide solution (3×150 mL), DI water (3×150 mL) and acetone (3×150 mL). The material was placed in an oven to dry at 40° C. for 12 hrs.

Obtained 2.52 g as a white fibrous solid.

Functional Performance of the Media.

The sulfopropyl-functionalized high surface area fibers from Example 26 were evaluated in a cation exchange chromatography media for the purification of the polyclonal human gamma immunoglobulin (IgG).

The results of static binding capacity measurements for IgG are provided in Table 27. In this study, the static binding capacity of a sample of the unfunctionalized "winged fiber" from Allaso (lot ID "3 kg batch—no manuf. lot ID") was compared to samples of sulfopropyl-tentacle functionalized fibers prepared by the ceric ion redox polymerization process of Example 26 and the thermally-initiated polymer grafting process described in Example 2. It was found that the ceric ion redox grafting procedure provided a SP-functionalized tentacle fiber media with a significantly higher static binding capacity (150 mg IgG/g fiber sample) than that of the thermally-initiated process (50 mg IgG/g fiber sample) and the unfunctionalized fibers alone (10 mg IgG/g fiber sample). The SP-functionalized tentacle fiber media demonstrates an IgG static binding capacity comparable to bead-based resin media employed in commercial biomolecule chromatography applications.

TABLE 27

Static binding capacity measurement. Challenge: 2 g/L polyclonal human IgG (SeraCare LifeSciences, Milford, MA) in 50 mM Sodium Acetate (pH 5).

| Sample ID | Process | Amt (g) | IgG bound (mg) | SBC (mg/g) |
|---|---|---|---|---|
| unfunctionalized Allasso #090602PA6C | — | 0.11 g | 1.0 | 10 |
| unfunctionalized Allasso #090602PA6C | — | 0.10 g | 1.0 | 10 |
| SP-funct. Allasso Example 26 | Ce(IV) grafting | 0.10 g | 16 | 160 |
| SP-funct. Allasso Example 26 | Ce(IV) grafting | 0.10 g | 14 | 140 |
| SP-funct. Allasso Example 2 | thermal graft | 0.12 g | 6.5 | 56 |
| SP-funct. Allasso Example 2 | thermal graft | 0.12 g | 5.8 | 50 |

HETP values were measured using acetone injections on a 11 mm ID Vantage column packed with 1.00 g of the SP-tentacle modified nylon fibers from Example 26 with a fiber bed compressed to a bed depth of 3.0 cm (column volume 2.85 ml). Acceptable values for HETP (0.08 cm) and peak asymmetry (1.8-2.0) were found. Based on these results, it is believed that a SP-tentacle modified fiber packing density of 0.35 g/mL will provide sufficient flow uniformity for acceptable performance in a chromatographic evaluation.

IgG dynamic binding capacity measurements were also performed with this same column according to the following procedure:

5 CV (column volume) 50 mM NaOAc buffer (pH 5) (Equilibration)
60 CV 1.7 mg/mL IgG (SeraCare) in 50 mM NaOAc buffer (pH 5) (IgG Challenge)
30 CV 50 mM NaOAc buffer (pH 5) (wash)
15 CV 1 M NaCl in 50 mM NaOAc buffer (pH 5) (elution)
10 CV 0.5 M NaOH (cleaning)
10 CV 50 mM NaOAc buffer (pH 5) (wash)

FIG. 10 provides an example of a typical IgG breakthrough curve for the SP-tentacle modified fibers in accordance with certain embodiments. There is a sharp breakthrough curve and IgG dynamic binding capacities of 40 mg/mL at 10% IgG breakthrough (Table 28).

TABLE 28

IgG dynamic binding capacities for the SP-tentacle functionalized Allasso winged fiber cation exchange media at 1, 5, 10 and 50% breakthrough at varying linear velocities (RT = residence time).

| % Breakthrough | DBC (mg/mL) | | | | | |
|---|---|---|---|---|---|---|
| | 200 cm/hr (RT 54 sec) | 200 cm/hr (RT 54 sec) | 200 cm/hr (RT 54 sec) | 400 cm/hr (RT 27 sec) | 800 cm/hr (RT 14 sec) | 1200 cm/hr (RT 9 sec) |
| 1 | 39 | 42 | 43 | 39 | 35 | 24 |
| 5 | 41 | 45 | 45 | 42 | 37 | 26 |
| 10 | 42 | 46 | 47 | 44 | 39 | 27 |
| 50 | 49 | 53 | 54 | 52 | 48 | 32 |

FIG. 11 provided overlaid IgG breakthrough curves for the SP-tentacle fiber column at varying linear velocities, ranging from 200 cm/hr to 1200 cm/hr. As linear flow velocity is increased, the slope of the IgG breakthrough curves is slightly decreased. The velocity effect on dynamic IgG binding capacity for the fiber media in accordance with embodiments disclosed herein is much less pronounced than what is typically observed in bead-based systems. In FIG. 12, only a modest decrease in the measured IgG dynamic binding capacity at the highest velocity measured (1200 cm/hr, 9 second residence time) is seen. This behavior is indicative of a system that is largely dominated by convective transport of IgG molecules to the ionic ligand binding site.

In contrast, traditional bead-based ion-exchange chromatography resins will show a significant decrease in dynamic binding capacity and more diffuse breakthrough curves as velocities are increased. At very high velocities, bed compression may compromise the integrity of the beads, resulting in poorer flow uniformity and decreased chromatographic performance.

Example 27

Flow-Through Host Cell Protein Clearance.

The sulfopropyl-functionalized fiber media prepared according to Example 26 was evaluated for HCP removal activity in a flow-through polishing mode. 0.3 g of the sulfopropyl-functionalized fiber media was packed into a 14.5 mm internal diameter column and compressed to a bed depth of 0.6 cm (1.00 mL column volume, 0.30 g/mL fiber packing density). The column was tested independently and in combination with commercial membrane adsorber (ChromaSorb™, Millipore Corp, membrane volume 0.2 mL).

A cell culture media containing monoclonal antibody was clarified and then isolated using Protein A column chromatography and the pH of the solution was adjusted to pH 5. The pH of the Protein A elution was subsequently adjusted to pH 7 with TRIS and then filtered through a 0.2 micron membrane.

The column and Chromasorb™ membrane device were equilibrated with a buffer solution (25 mM Tris at pH 7).

The sulfopropyl-functionalized fiber media and Chromasorb™ membrane adsorber were evaluated individually and in series as described in Table 29. 72 mL of the 7.3 g/L monoclonal antibody Protein A elution (pH 7) was passed through the devices at a flow rate of 0.25 mL/min. Six 12 mL factions were collected. The eight flow-through fractions as well as a pooled sample were analyzed by HCP-ELISA and protein A HPLC to determine the level of HCP clearance and the monoclonal antibody recovery, respectively.

While the SP-fibers (0.38 LRV) did not remove as much HCP as the ChromaSorb™ membrane adsorber (1.42 LRV), we found that the arrangement of the two flow-though adsorbers in series at pH 7 was more effective at HCP clearance (2.13 LRV) than either adsorber individually. Since these adsorber media are not capacity limited in this application, these results suggest that the two adsorbers are removing separate and distinct populations of HCP. We suspect that the SP-fibers would remove more HCP at a lower pH where the HCP would have a more positive effective charge, however, affinity of the monoclonal antibody for the SP-fibers would also be increased and would reduce the product recovery.

TABLE 29

Flow through purification of a monoclonal antibody feed. Evaluation of three flow through polishing trains. SP-fibers (Example 26) (top), ChromaSorb ™ (middle), SP-fiber (Example 26)/ChromaSorb ™ arranged in series (bottom). Monoclonal antibody recovery (Protein A HPLC) and HCP clearance (HCP-ELISA) for 5 flow through and 1 pooled fraction. Challenge: 7.3 g/L of a monoclonal antibody Protein A elution (pH 7) at a flow rate of 0.25 mL/min.

| Adsorber 1 | Adsorber 2 | Sample # | Volume Collected (mL)[1] | mAb (mg/mL) | Recovery mAb | HCP (ng/mL) | HCP (ppm) | HCP LRV |
|---|---|---|---|---|---|---|---|---|
| — | — | Protein A elution feed | — | 7.31 | — | 616 | 84 | — |
| SP-fibers (Example 26) | — | Fraction 1 | 12 | 5.08 | 70% | 128 | 25 | |
| | | Fraction 2 | 24 | 7.52 | 103% | 276 | 37 | |
| | | Fraction 3 | 36 | 7.49 | 102% | 272 | 36 | |
| | | Fraction 4 | 48 | 6.87 | 94% | 294 | 43 | |
| | | Fraction 5 | 72 | 6.70 | 92% | 243 | 36 | |
| | | Pool | — | 6.59 | 90% | 257 | 39 | 0.38 |
| ChromaSorb ™ | — | Fraction 1 | 12 | 7.09 | 97% | 18 | 2 | |
| | | Fraction 2 | 24 | 7.14 | 98% | 22 | 3 | |
| | | Fraction 3 | 36 | 7.10 | 97% | 27 | 4 | |

TABLE 29-continued

Flow through purification of a monoclonal antibody feed. Evaluation of three flow through polishing trains. SP-fibers (Example 26) (top), ChromaSorb ™ (middle), SP-fiber (Example 26)/ChromaSorb ™ arranged in series (bottom). Monoclonal antibody recovery (Protein A HPLC) and HCP clearance (HCP-ELISA) for 5 flow through and 1 pooled fraction. Challenge: 7.3 g/L of a monoclonal antibody Protein A elution (pH 7) at a flow rate of 0.25 mL/min.

| Adsorber 1 | Adsorber 2 | Sample # | Volume Collected (mL)[1] | mAb (mg/mL) | Recovery mAb | HCP (ng/mL) | HCP (ppm) | HCP LRV |
|---|---|---|---|---|---|---|---|---|
| | | Fraction 4 | 48 | 7.62 | 104% | 26 | 3 | |
| | | Fraction 5 | 72 | 7.14 | 98% | 31 | 4 | |
| | | Pool | — | 7.29 | 100% | 24 | 3 | 1.42 |
| SP-fibers (Example 26) | ChromaSorb ™ | Fraction 1 | 12 | 4.61 | 63% | 1 | 0 | |
| | | Fraction 2 | 24 | 7.63 | 104% | 3 | 0 | |
| | | Fraction 3 | 36 | 7.11 | 97% | 5 | 1 | |
| | | Fraction 4 | 48 | 6.82 | 93% | 6 | 1 | |
| | | Fraction 5 | 72 | 6.40 | 88% | 9 | 1 | |
| | | Pool | — | 7.05 | 96% | 5 | 1 | 2.13 |

[1]Aggregate total of flow through fraction volumes

Example 28

Flow-Through Host Cell Protein Clearance.

The Q-functionalized fiber media prepared according to Example 14 (entry Example 14C) was evaluated for HCP removal activity in a flow-through polishing mode. 0.34 g of the Q-functionalized fiber media was packed into a 14.5 mm internal diameter column and compressed to a bed depth of 0.6 cm (1.00 mL column volume, 0.34 g/mL fiber packing density).

A cell culture media containing monoclonal antibody was clarified and then isolated using Protein A column chromatography and the pH of the solution was adjusted to pH 5. The pH of the Protein A elution was subsequently adjusted to pH 8 with TRIZMA base and then filtered through a 0.2 micron membrane.

The Q-functionalized fiber media column was equilibrated with a buffer solution (25 mM Tris at pH 8).

Data from the evaluation of the Q-functionalized fiber media is provided in Table 30. 100 mL of 8.2 g/L monoclonal antibody Protein A elution (pH 8) was passed through the devices at a flow rate of 1.0 mL/min. Ten 10 mL factions were collected. Bound HCP was eluted using a 1 M sodium chloride solution in 25 mM Tris pH 8 as an elution buffer. Two 10 mL elution fractions were also collected. The ten flow-through fractions and two elution fractions were analyzed by HCP-ELISA and protein A HPLC to determine the level of HCP clearance and the monoclonal antibody recovery, respectively.

The Q-functionalized fibers were effective at HCP clearance in a flow through mode. An HCP LRV of 0.3 was achieved with high mAb recovery (94%). The Q-functionalized fiber media of the embodiments disclosed herein may serve as a convenient, low cost alternative to bead-based resin media and membrane adsorber systems for flow through polishing applications in monoclonal antibody production. The high permeability of the Q-functionalized fiber media (700 mDa for a Q-functionalized fiber media prepared according to Example 14C) may enable the high speed processing of mAb feed streams at flow rates not attainable using membrane adsorbers.

TABLE 30

Flow through purification of a monoclonal antibody feed. Evaluation of a flow through polishing process comprising Q-functionalized fiber media in a packed bed format (1.0 mL column volume, 0.34 g/mL packing density). Monoclonal antibody recovery (Protein A HPLC) and HCP clearance (HCP-ELISA) for 5 flow through and 2 elution fractions. The pooled fraction data are calculated values. Challenge: 8.2 g/L of a monoclonal antibody Protein A elution (pH 8) at a flow rate of 1.0 mL/min (residence time = 60 seconds).

| Adsorber | Sample # | Volume Collected (mL)[1] | mAb (mg/mL) | Recovery mAb | HCP (ng/mL) | HCP (ppm) | HCP LRV |
|---|---|---|---|---|---|---|---|
| — | Protein A elution feed | — | 8.2 | — | 6459 | 790 | — |
| Q-fibers (Example 14C) | Fraction 1 | 10 | 4.3 | 52% | 1472 | 344 | |
| | Fraction 2 | 20 | 8.1 | 98% | 3822 | 474 | |
| | Fraction 3 | 30 | 8.1 | 99% | 3161 | 389 | |
| | Fraction 4 | 40 | 8.1 | 99% | 4022 | 496 | |
| | Fraction 5 | 50 | 8.1 | 99% | 3189 | 392 | |
| | Fraction 6 | 60 | 8.1 | 99% | 3352 | 412 | |
| | Fraction 7 | 70 | 8.1 | 99% | 3359 | 412 | |
| | Fraction 8 | 80 | 8.1 | 99% | 3405 | 419 | |
| | Fraction 9 | 90 | 8.1 | 99% | 3519 | 434 | |
| | Fraction 10 | 100 | 8.1 | 99% | 3141 | 386 | |
| | Pool | — | 7.7 | 94% | 3244 | 421 | 0.3 |
| | Elution 1 | 10 | 0.7 | — | 28540 | 42900 | |
| | Elution 2 | 20 | 0.0 | — | 632 | 0 | |

[1]Aggregate total of flow through and elution fraction volumes

Example 29

Flow-Through Monoclonal Antibody Aggregate Clearance.

The sulfopropyl-functionalized fiber media prepared according to Example 26 was evaluated for monoclonal antibody aggregate removal activity in a flow-through polishing mode. 1.0 g of the sulfopropyl-functionalized fiber media was packed into a 11 mm internal diameter Vantage column and compressed to a bed depth of 3.0 cm (2.85 mL column volume, 0.35 g/mL fiber packing density).

A Protein A elution pool containing 20 g/L monoclonal antibody was diluted with a solution of 0.5° M sodium chloride in 50 mM acetate buffer (pH 5) and 50 mM acetate buffer (pH 5) to provide a 6.9 g/L solution at pH 5 and a conductivity of 19 mS/cm. A conductivity value of 19 mS/cm was selected in order to weaken the binding of monomeric monoclonal antibody and to favor the binding of aggregated monoclonal antibody species in the protein A feed solution.

The sulfopropyl-functionalized fiber media column was equilibrated with a buffer solution (50 mM acetate at pH 5).

Data from the evaluation of the sulfopropyl-functionalized fiber media is provided in Table 31 and FIG. 9. 285 mL of 6.9 g/L monoclonal antibody Protein A elution (pH 5, 19 mS/cm) was passed through the column at a flow rate of 3.2 mL/min (200 cm/hr). Thirty-three 8.6 mL (3 column volume) factions were collected. Bound monomeric and aggregated monoclonal antibody was eluted using a 0.5 M sodium chloride solution in 50 mM acetate pH 5 as an elution buffer. Five 8.6 mL (3 column volume) elution fractions were also collected. The thirty-three flow-through fractions and five elution fractions were analyzed by size exclusion chromatography (SEC) and protein A HPLC to determine the level of aggregate clearance and the monoclonal antibody recovery, respectively.

The sulfopropyl functionalized-fibers demonstrated an ability to bind aggregated monoclonal antibody in the presence of monomeric monoclonal antibody species under a flow through mode of operation. From the Protein A HPLC data we find a high mAb recovery of 92%. Analysis of the SEC data shows a complete breakthrough of the monomeric mAb species in flow through fraction #2, while the aggregated mAb does not match the initial feed concentration of 0.6% (100% breakthrough) until flow through fraction #5. SEC analysis of the elution fractions #35, 36, and 37 show a mAb population enriched in the aggregated high molecular weight (HMW) species and depleted in monomeric mAb. The sulfopropyl-functionalized fiber media in accordance with the embodiments disclosed herein may serve as a means for aggregate clearance according to the method described in the present example. The high permeability of the sulfopropyl-functionalized fiber media (520 mDa for a sulfopropyl-functionalized fiber media prepared according to Example 26) may enable the high speed, rapid cycling of mAb feed streams at high flow rates suitable for simulated moving bed operations.

TABLE 31

Flow through aggregate clearance of a monoclonal antibody feed. Evaluation of a flow through aggregate clearance process comprising sulfopropyl-functionalized fiber media in a packed bed format (2.85 mL column volume, 0.35 g/mL packing density). Monoclonal antibody recovery (Protein A HPLC) and % monomer, % HMW aggregate (SEC) for 31 flow through and 3 elution fractions. The pooled fraction data are calculated values. Challenge: 6.9 g/L of a monoclonal antibody Protein A elution (pH 5, 19 mS) at a flow rate of 3.2 mL/min (residence time = 54 seconds).

| Adsorber | Sample # | Volume Collected (mL)[1] | mAb (mg/mL) | Recovery mAb | % monomer (SEC) | % HMW aggregate (SEC) |
|---|---|---|---|---|---|---|
| — | Protein A elution feed | — | 6.9 | — | 99.1 | 0.6 |
| sulfopropyl-fibers (Example 26) | Fraction 1 | 8.6 | 0.0 | 0% | 0.0 | 0.0 |
| | Fraction 2 | 17 | 5.0 | 73% | 99.6 | 0.0 |
| | Fraction 3 | 26 | 7.0 | 102% | 99.4 | 0.4 |
| | Fraction 5 | 43 | 6.8 | 100% | 99.1 | 0.6 |
| | Fraction 7 | 60 | 6.9 | 100% | 99.1 | 0.6 |
| | Fraction 9 | 77 | 6.9 | 100% | 99.1 | 0.6 |
| | Fraction 11 | 95 | 6.9 | 100% | 99.1 | 0.6 |
| | Fraction 13 | 112 | 6.9 | 100% | 99.1 | 0.6 |
| | Fraction 15 | 129 | 6.8 | 100% | 99.1 | 0.6 |
| | Fraction 17 | 146 | 6.9 | 100% | 99.1 | 0.6 |
| | Fraction 19 | 163 | 6.8 | 100% | 99.1 | 0.6 |
| | Fraction 21 | 181 | 6.9 | 100% | 99.1 | 0.6 |
| | Fraction 23 | 198 | 6.9 | 100% | 99.1 | 0.6 |
| | Fraction 25 | 215 | 6.9 | 100% | 99.1 | 0.6 |
| | Fraction 27 | 232 | 6.9 | 100% | 99.1 | 0.6 |
| | Fraction 31 | 267 | 6.9 | 100% | 99.1 | 0.6 |
| | Pool | — | 6.3 | 92% | 99.1 | 0.5 |
| | Elution 35 | 8.6 | 2.3 | — | 2.7 | 95.1 |
| | Elution 36 | 17 | 1.5 | — | 8.2 | 87.6 |
| | Elution 37 | 26 | 0.1 | — | 0.0 | 100 |

[1]Aggregate total of flow through and elution fraction volumes

Example 32

Direct Capture on a Compressible Bed.

The sulfopropyl-functionalized fiber media of Example 19 was evaluated for direct monoclonal antibody capture from an unclarified cell culture fluid in a flow-through mode of operation. 0.49 g of the sulfopropyl-functionalized fiber media was packed into a 14.5 mm internal diameter column and compressed to a bed depth of 3.0 cm (5.0 mL column volume, 0.10 g/mL fiber packing density). The sulfopropyl-functionalized fiber media column was equilibrated with a buffer solution (50 mM acetate at pH 5). An unclarified Chinese Hamster Ovary cell culture fluid containing 0.8 g/L monoclonal antibody was provided (pH 6.5, 5.7 mS/cm).

100 mL of the unclarified cell culture fluid containing 0.8 g/L monoclonal antibody was passed through the column at a flow rate of 12.5 mL/min (460 cm/hr). Nine 10 mL (2 column volume) flow through factions were collected. The low density fiber bed was washed with 50 mM acetate buffer (pH 5) by repeated compression and expansion of the fiber bed. This compression and expansion was accomplished by adjustment of the column flow distribution header. Thirteen 10 mL (2 column volume) 50 mM acetate buffer (pH 5) washing factions were collected. Bound monoclonal antibody was eluted using a 1.0 M sodium chloride solution in 50 mM acetate pH 5 as an elution buffer. It is preferable to accomplish the elution step in a compressed bed format (bed depth 1.0 cm, 1.65 mL column volume, 0.30 g/mL fiber packing density) in order to further concentrate the monoclonal antibody elution. Three 10 mL (2 column volume) elution fractions were collected. The nine flow-through fractions, thirteen washing fractions and three elution fractions were analyzed by protein A HPLC to measure the monoclonal antibody recovery. Data from the evaluation of the sulfopropyl-functionalized fiber media is provided in Table 32.

The sulfopropyl-functionalized fibers demonstrated an ability to bind monoclonal antibody (mAb) in the presence of unclarified Chinese hamster ovary cell culture media. From the Protein A HPLC data, we find complete mAb breakthrough during the mAb capture operation by Fraction #7. The 50 mM acetate (pH 5) washing stage removes any unbound mAb from the column and the system by wash fraction #6. Elution with 1.0 M sodium chloride in 50 mM acetate (pH 5) elutes the bound mAb from the sulfopropyl-functionalized fiber media column. Those skilled in the art will recognize that significant gains in monoclonal IgG binding capacity may be realized by any number of process variations. These may include the reduction of cell culture feed conductivity, dilution of the unclarified cell culture feed, or the use of a Protein A affinity ligand structure instead of the sulfopropyl-based cation exchange ligand functionality of the present example. Those skilled in the art will recognize that the Protein A functionalized fiber media of Example 18, or its derivatives, may be preferred for this direct capture application. In a low packing density format, the surface functionalized fiber media is capable of direct IgG capture from unclarified feed streams. A subsequent bed compression enables the concentration of the mAb elution in a compressed bed format. This process may eliminate the use of primary (centrifugation) and secondary clarification (depth filtration) processes in the downstream processing of therapeutic biopharmaceuticals such as monoclonal antibodies.

TABLE 32

Direct capture of a monoclonal antibody from unclarified cell culture. Evaluation of a direct mAb capture process comprising sulfopropyl-functionalized fiber media in a packed bed format (5.00 mL column volume, 0.10 g/mL packing density). Monoclonal antibody concentration and recovery (Protein A HPLC) for 4 flow through, 4 wash and 3 sodium chloride elution fractions. Challenge: 100 mL of an unclarified Chinese hampster ovary cell culture fluid containing 0.87 g/L of monoclonal antibody (pH 6.5, 5.7 mS) at a flow rate of 12.5 mL/min (residence time = 24 seconds).

| Adsorber | Sample # | Volume Collected (mL)[1] | mAb (mg/mL) | mAb $C/C_o$ | mAb recovery (mg) |
|---|---|---|---|---|---|
| — | unclarified mAb feed | — | 0.87 | | |
| sulfopropyl-fibers (Example 19) | Fraction 2 | 20 | 0.0 | 0.0 | |
| | Fraction 5 | 50 | 0.26 | 0.30 | |
| | Fraction 7 | 70 | 0.90 | 1.03 | |
| | Fraction 9 | 90 | 0.85 | 0.98 | |
| | Wash 2 | 20 | 0.86 | 0.99 | 8.6 |
| | Wash 6 | 60 | 0.0 | 0.0 | 0.0 |
| | Wash 10 | 100 | 0.0 | 0.0 | 0.0 |
| | Wash 13 | 130 | 0.0 | 0.0 | 0.0 |
| | Elution 1 | 10 | 0.76 | 0.87 | 7.6 |
| | Elution 2 | 20 | 0.21 | 0.24 | 2.1 |
| | Elution 3 | 30 | 0.06 | 0.07 | 0.6 |

[1]Aggregate total of flow through, wash and elution fraction volumes

Example 33

Fiber Media Capability for the Bind/Elute Purification of Viruses.

The results of static binding capacity and elution recovery measurements for bacteriophage φ6 are provided in Table 31 below. Into 5 plastic centrifuge tubes were added the Q-functionalized tentacle fiber media of Example 14C and unfunctionalized Allasso fiber samples in the amounts described in Table 33 below. Each of the fiber samples and the control tube were equilibrated with 5 mL of 25 mM Tris buffer (pH 8, with 0.18 mg/mL HSA) with agitation for 10 minutes. The tubes were spun at room temperature in a table top centrifuge at 4000 rpm for 10 minutes to pellet the fiber media. 2.5 mL of the supernatant was removed and 2.5 mL of a $1.7 \times 10^7$ pfu/mL φ6 solution in 25 mM Tris buffer (pH 8, with 0.18 mg/mL HSA) were added to each tube. The samples were agitated at room temperature for 1 hour. Afterwards, the tubes were spun at room temperature in a table top centrifuge at 4000 rpm for 15 minutes to pellet the fiber media. 2.5 mL of the supernatant was removed and these samples were assayed for unbound φ6 by plaque-forming assay. The tubes were washed 3 times with 2.5 mL washings of 25 mM Tris buffer (pH 8, with 0.18 mg/mL HSA) with centrifugation to pellet the fiber media in between each wash and removal of 2.5 mL of the supernatant. After washing, 2.5 mL of a 1.0 M NaCl solution in 25 mM Tris buffer (pH 8, with 0.18 mg/mL HSA) were added to each tube (5 mL total volume, final NaCl concentration is 0.5 M). The samples were agitated at room temperature for 10 minutes. Afterwards, the tubes were spun at room temperature in a table top centrifuge at 4000 rpm for 10 minutes to pellet the fiber media. 2.5 mL of the supernatant was removed and these elution samples were assayed for eluted φ6 by plaque forming assay. The Q-functionalized tentacle fiber media of example 14C demonstrates a significant bacteriophage φ6 log reduction value (LRV) of 3.1 and an elution recovery yield of 40%. This performance is comparable to membrane-based anion-exchange media employed in commercial viral chromatography applications. The Q-functionalized fiber media of the present invention can be integrated into a prepacked device format or a chromatography column for flow-through viral clearance or bind/elute viral purification applications.

TABLE 33

Static binding capacity measurement. Challenge: 2.5 mL of $1.7 \times 10^7$ pfu/mL bacteriophage φ6 in 25 mM Tris (pH 8) with 0.18 mg/mL HSA. Elution buffer: 0.5M NaCl in 25 mM Tris (pH 8) with 0.18 mg/mL HSA.

| Sample | Amt (g) | φ6 titer (pfu/mL) | φ6 bound (LRV) | Elution φ6 titer (pfu/mL) | % recovery, φ6 |
|---|---|---|---|---|---|
| Control Tube | — | $2.10 \times 10^7$ | — | $2.15 \times 10^6$ | — |
| Example 14C | 0.051 g | $1.39 \times 10^4$ | 3.18 | $8.45 \times 10^6$ | 40.3% |
| Example 14C | 0.052 g | $1.65 \times 10^4$ | 3.10 | $8.15 \times 10^6$ | 38.8% |
| Allasso non-functionalized fibers | 0.051 g | $2.09 \times 10^7$ | 0.00 | $8.65 \times 10^5$ | — |
| Allasso non-functionalized fibers | 0.050 g | $2.32 \times 10^7$ | −0.04 | $7.10 \times 10^5$ | — |

What is claimed is:

1. A non-woven bed of fibers having a cross-section comprising a body region defining a substantially longitudinal axis, and having a plurality of projections extending outwardly from said body region, said fibers having imparted thereon functionality enabling ion-exchange chromatography.

2. A housing comprising a packed bed of loose or fused cut fibers having a cross-section comprising a body region defining a substantially longitudinal axis, and having a plurality of projections extending outwardly from said body region, said fibers having imparted thereon functionality enabling ion-exchange chromatography.

3. A process for purifying proteins, comprising;
providing a protein mixture,
contacting said protein mixture with a bed of fibers having a cross-section comprising a body region defining a substantially longitudinal axis, and having a plurality of projections extending outwardly from said body region, said fibers having imparted thereon functionality enabling a chromatography selected from the group consisting of ion-exchange functionality, hydrophobic interaction, and affinity chromatography,
washing said fiber media to remove unbound species,
compressing said fiber media, and
washing said compressed fiber media to extract bound protein.

4. Chromatography media comprising fibers having a cross-section comprising a region comprising a body region defining a substantially longitudinal axis, and a plurality of projections extending outwardly from said body region, said fibers having imparted thereon anion-exchange functionality.

5. Chromatography media comprising fibers having a cross-section comprising a region comprising a body region defining a substantially longitudinal axis, and a plurality of projections extending outwardly from said body region, said fibers having imparted thereon acrylic polymer functionality.

6. Chromatography media comprising fibers having a cross-section comprising a region comprising a body region defining a substantially longitudinal axis, and a plurality of projections extending outwardly from said body region, said fibers having imparted thereon functionality enabling cation-exchange chromatography, wherein the surfaces of said fibers are modified with pendant sulfopropyl groups.

7. Chromatography media comprising fibers having a cross-section comprising a region comprising a body region defining a substantially longitudinal axis, and a plurality of projections extending outwardly from said body region, said fibers having imparted thereon functionality enabling anion-exchange chromatography, wherein the surfaces of said fibers are modified with pendant trimethylammonium groups.

8. A housing comprising a packed bed of fibers having a cross-section comprising a region comprising a body region defining a substantially longitudinal axis, and a plurality of projections extending outwardly from said body region, said fibers having imparted thereon anion-exchange functionality, cation-exchange functionality, or acrylic polymer functionality.

9. The process of claim 3, wherein said protein comprises a monoclonal antibody.

* * * * *